(12) United States Patent
Bamberg et al.

(10) Patent No.: US 11,384,132 B2
(45) Date of Patent: Jul. 12, 2022

(54) MUTANT LIGHT-INDUCIBLE ION CHANNEL OF CHRIMSON

(71) Applicants: Max-Planck-Gesellschaft zur Förderung der Wissenschaften e.V., Munich (DE); Georg-August-Universität Göttingen Stiftung Öffentlichen Rechts, Universitätsmedizin, Goettingen (DE)

(72) Inventors: Ernst Bamberg, Kelkheim (DE); Phil Wood, Schmelz/Saar (DE); Thomas Mager, Frankfurt (DE); Tobias Moser, Goettingen (DE); David Lopez de la Morena, Goettingen (DE)

(73) Assignees: Max-Planck-Gesellschaft zur Förderung der Wissenschaften e.V.; Georg-August-Universität Göttingen Stiftung Öffentlichen Rechts, Universitätsmedizin

(*) Notice: Subject to any disclaimer, the term of this patent is extended or adjusted under 35 U.S.C. 154(b) by 369 days.

(21) Appl. No.: 16/306,652

(22) PCT Filed: Jun. 2, 2017

(86) PCT No.: PCT/EP2017/063458
§ 371 (c)(1),
(2) Date: Dec. 3, 2018

(87) PCT Pub. No.: WO2017/207761
PCT Pub. Date: Dec. 7, 2017

(65) Prior Publication Data
US 2019/0218271 A1 Jul. 18, 2019

(30) Foreign Application Priority Data
Jun. 3, 2016 (EP) .................... 16172984

(51) Int. Cl.
*C07K 14/705* (2006.01)
*C07K 14/405* (2006.01)
(Continued)

(52) U.S. Cl.
CPC .......... *C07K 14/705* (2013.01); *A61K 9/0019* (2013.01); *A61P 27/02* (2018.01);
(Continued)

(58) Field of Classification Search
None
See application file for complete search history.

(56) References Cited

U.S. PATENT DOCUMENTS
2016/0039902 A1   2/2016   Klapoetke et al.

FOREIGN PATENT DOCUMENTS
JP   2013544494      3/2021
WO   2003084994 A2   10/2003
(Continued)

OTHER PUBLICATIONS

Nagel, G. et al., Channelrhodopsin-2, a directly light-gated cation-selective membrane channel. Proc Natl Acad Sci USA 100, 13940-13945 (2003).
(Continued)

*Primary Examiner* — Aurora M Fontainhas
(74) *Attorney, Agent, or Firm* — Williams Mullen; David M. Saravitz

(57) ABSTRACT

The invention relates to mutant light-inducible ion channels having improved properties as compared to the parent channel, nucleic acid constructs encoding same, expression vectors carrying the nucleic acid construct, cells comprising the nucleic acid construct or expression vector, and their respective uses, as well as non-human animals comprising
(Continued)

the mutant light-inducible ion channel, the nucleic acid construct or the expression vector as disclosed herein.

17 Claims, 6 Drawing Sheets

Specification includes a Sequence Listing.

(51) Int. Cl.
  A61P 27/02 (2006.01)
  A61K 9/00 (2006.01)
  C12N 5/079 (2010.01)
  C12N 15/86 (2006.01)
  G01N 33/68 (2006.01)
(52) U.S. Cl.
  CPC .......... C07K 14/405 (2013.01); C12N 5/0621 (2013.01); C12N 15/86 (2013.01); G01N 33/6872 (2013.01)

(56) References Cited

FOREIGN PATENT DOCUMENTS

WO 2012032103 A1 3/2012
WO 2013071231 A1 5/2013

OTHER PUBLICATIONS

Nagel, G. et al., Light activation of channelrhodopsin-2 in excitable cells of Caenorhabditis elegans triggers rapid behavioral responses. Curr Biol 15, 2279-2284 (2005).
Boyden, E., Zhang, F., Bamberg, E., Nagel, G. & Deisseroth, K., Millisecond-timescale, genetically targeted optical control of neural activity. Nat Neurosci 8, 1263-1268 (2005).
Zhang, F. et al., Multimodal fast optical interrogation of neural circuitry. Nature 446, 633-639 (2007).
Nagel, G. et al., Channelrhodopsin-1: A Light-Gated Proton Channel in Green Algae. Science. 296, 2395-2398 (2002).
Bamann, C., Gueta, R., Kleinlogel, S., Nagel, G. & Bamberg, E., Structural guidance of the photocycle of channelrhodopsin-2 by an interhelical hydrogen bond. Biochemistry 49, 267-278 (2010).
Berndt, A., Yizhar, O., Gunaydin, L., Hegemann, P. & Deisseroth, K., Bi-stable neural state switches Nat Neurosci 12, 229-234 (2009).
Lin, J., Lin, M., Steinbach, P. & Tsien, R., Characterization of engineered channelrhodopsin variants with improved properties and kinetics. Biophys J 96, 1803-1814 (2009).
Klapoetke N. et al., Independent optical excitation of distinct neural populations. Nature Methods. 11, 338-346 (2014).
Allocca, M. et al., Novel adeno-associated virus serotypes efficiently transduce murine photoreceptors. J Virology 81, 11372-11380 (2007).
Hernandez et al., Optogenetic stimulation of the auditory pathway. J Clin Invest. 124(3): 1114-1129 (2014).
Liberman, M.C., Auditory-nerve response from cats raised in a low-noise chamber. J. Acoust. Soc. Am. 63,442-455 (1978).
Winter, I.M., Robertson, D., and Yates, G.K., Diversity of characteristic frequency rate-intensity functions in guinea pig auditory nerve fibres. Hear. Res. 45, 191-202 (1990).
Macé et al., Targeting channelrhodopsin-2 to ON-bipolar cells with vitreally administered AAV Restores ON and OFF visual responses in blind mice. Mol Ther. 23(1): 7-16 (2015).
Müller, M., Bamann, C., Bamberg, E. & Kuhlbrandt, W., Light-induced helix movements in channelrhodopsin-2. J Mol Biol 427, 341-349, doi:10 1016/j.jmb.2014.11.004 (2015).
Lin J. Y. et al., ReaChR: a red-shifted variant of channelrhodopsin enables deep transcranial optogenetic excitation. Nature Neuroscience. 16, 1499-1508 (2013).
Kato, H. E. et al., Crystal structure of the channelrhodopsin light-gated cation channel. Nature 482, 369-374, doi:10.1038/nature10870 (2012).
Volkov, O. et al., Structural insights into ion conduction by channel rhodopsin 2. Science 358, eaan8862, DOI:10.1126/science.aan8862(2017).
Mager, T. et al., High frequency neural spiking and auditory signaling by ultrafast red-shifted optogenetics. Nat Commun. 9: 1750, DOI: 10.1038/s41467-018-04146-3(2018).
Oda, K. et al. Crystal structure of the red light-activated channelrhodopsin Chrimson. Nat Commun. 9: 3949, DOI: 10.1038/s41467-018-06421-9(2018).
Tsunoda et al, "Glu 87 of Channelrhodopsin-1 Causes pH-dependent Color Tuning and Fast Photocurrent Inactivation",Photochemistry and Photobiology, 2009, 85, pp. 564-569.
Japanese Patent Office, Japanese Examination Report for Japanese Patent Application No. 2019-516075; dated Jul. 27, 2021.
Berndt et al, "High-efficiency channelrhodopsins for fast neuronal stimulation at low light levels," PNAS, 2011, pp. 7595-7600, vol. 108 (18).
Lin et al, "A user's guide to channelrhodopsin variants: features, limitations and future developments," Exp Physiol, 2010, pp. 19-25, vol. 96(1).
Database ENA (Online), Jan. 30, 2014, "Synthetic Construct Protein '92", XP002762998, retrieved from EBI accession No. EMBL: AHH02115.
Database Geneseq (Online), Jul. 3, 2014, "Chlamydomonas raudensis Channelrhodopsin 2 (CrChR2) domain, SEQ ID 4", XP002762071, retrieved from EBI accession No. GSP: BBG24810.
Database Geneseq (Online), Nov. 19, 2015, "Chlamydomonas rheinhartii opsin ReaChR protein, SEQ 23", XP002762072, retrieved from EBI accession No. GSP: BCE86299.
Klapoetke, et al., "Independent optical excitation of distinct neural populations", Nature Methods, vol. 11, No. 3, Feb. 9, 2014, pp. 338-346.
Schneider, et al., "Design and electrophysiological characterization of rhodopsin-based optogenetic tools (Dissertation)", Mar. 21, 2014, pp. FP-158, XP002762073, retrieved from the Internet: URL:http://edoc.hu-berlin.de/dissertationen/schneider-franziska-2014-03-21/PDF/schneider.pdf.
International Search Report and Written Opinion for PCT/EP2017/063458, EPO, dated Aug. 2, 2017.

MUTANT LIGHT-INDUCIBLE ION CHANNEL OF CHRIMSON

CROSS-REFERENCE TO RELATED APPLICATIONS

This application is the U.S. National Stage of International Application PCT/EP2017/063458, filed Jun. 2, 2017, which designates the U.S. and was published by the International Bureau in English on Dec. 7, 2017, and which claims the benefit of European Patent Application No. 16172984.3, filed Jun. 3, 2016; both of which are hereby incorporated herein in their entirety by reference.

The invention relates to mutant light-inducible ion channel having improved properties as compared to the parent light-inducible ion channel, nucleic acid constructs encoding same, expression vectors carrying the nucleic acid construct, cells comprising said nucleic acid construct or expression vector, and their respective uses, as further defined in the claims.

BACKGROUND OF THE INVENTION

The light-gated, inwardly rectifying cation channels, channelrhodopsin-1 (ChR1) and channelrhodopsin 2 (ChR2) has become a preferred tool for the targeted light-activation of neurons both in vitro and vivo[1-5]. Although wild-type (WT) ChR2 can be employed for light-induced depolarization, there is an ongoing search for ChR2 mutants with faster kinetics and increased light-sensitivity for potential future clinical applications (WO 03/084994 and[6-8]).

Since the first description in 2002 and 2003 a set of different variants of ChR2 including a red-light absorbing channelrhodopsin are described. For different purposes ChR's were modified with respect to the kinetics, ion selectivity as well as light absorption. Examples are the red light absorbing channelrhodopsin from *Chlamydomonas* Chrimson (WO 2013/071231 and[9]; accession number KF992060), the Chrimson variant ChrimsonR (K176R), and CsChrimson, a chimeric polypeptide comprising the amino acid sequence from *Chlamydomonas* Chrimson, and an amino acid sequence derived from a Chloromonas channelrhodopsin CsChR, See also SEQ ID NOs: 1, 2, and 5 of US 2016/0039902, and accession number KJ995863. Red light activated channelrhodopsins are beneficial, because the penetration depths of red light into animal tissues is deeper than the penetration depths of lower wavelength light ([3,8]). Moreover the use of red light activated channelrhodopsins reduces the risk of phototoxicity.

The kinetics are a major issue, because the light sensitivity is regulated via the open time of the channel. This is due to the invariance of other channel parameters like single channel conductance, open probability, quantum efficiency. In other words, channels with a long open time reach the maximal activity at low light intensity, whereas short living channels need more light to reach saturation with respect to light saturation. Although 'fast' channels need more light for the activation, high speed is indispensable for many applications in neurobiology because of the high frequency firing rate of different neuronal cells. This is valid e.g. for ganglion cells in the auditory system for interneurons in the brain, which reach firing rates up to 1000 Hz. Accordingly, there is still a need for mutant light-inducible ion channels combining robust expression and faster response kinetics.

SUMMARY OF THE INVENTION

The inventors performed a systematic study on Chrimson by modifications in helix 6 of the seven transmembrane helix motif. Helix 6 movement during light-activation is a common feature in microbial-type rhodopsins ([15,17]). Therefore helix 6 was modified in order to change the closing time of the channel. It could be demonstrated that mutation of positions 261, 267, and 268 in helix 6 in Chrimson accelerates the closing time (off-kinetics) of the channel and that the combination of the mutations leads to a further acceleration of the off-kinetics.

The present disclosure describes a general way to modify Chrimson with respect to speed by specific point mutations in helix 6. The use of these new variants will provide a light stimulation of neurons up to their limits of 800 to 1000 Hz.

An experimental verification for the increased speed was tested in NG108-15 cells (neuroblastoma cells), in HEK293 cells, and hippocampal cells from the mouse brain.

Accordingly, disclosed is a mutant light-inducible ion channel, wherein the mutant light-inducible ion channel comprises an amino acid sequence which has at least 90% similarity/homology and/or at least 72% identity to the full length sequence of SEQ ID NO: 1 (Chrimson), and wherein the mutant light-inducible ion channel only differs from its parent light-inducible ion channel by a substitution at one or more position(s) selected from the positions corresponding to Y261, Y268, and S267 in SEQ ID NO: 1, which substitution(s) accelerate(s) the off-kinetics of the mutant channel as compared to the parent channel, when compared by patch-clamp measurements in the whole cell configuration at a clamp potential of −60 mV, a bath solution of 140 mM NaCl, 2 mM $CaCl_2$, 2 $MgCl_2$, 10 mM HEPES, pH 7.4, and a pipette solution of 110 mM NaCl, 2 mM $MgCl_2$, 10 mM EGTA, 10 mM HEPES, pH 7.4.

Further provided is a nucleic acid construct, comprising a nucleotide sequence coding for the light-inducible ion channel as disclosed herein.

Also provided is an expression vector, comprising a nucleotide sequence coding for the light-inducible ion channel or the nucleic acid construct as disclosed herein. Moreover, a cell is provided, comprising the nucleic acid construct or the expression vector as disclosed herein.

In still another aspect, the invention provides the use of the light-inducible ion-channel disclosed herein in a high-throughput screening, and/or for stimulating neurons. The use of the mutant light-inducible ion channel in medicine is also contemplated.

DETAILED DESCRIPTION OF THE PREFERRED EMBODIMENTS

The present disclosure pertains to mutant light-inducible ion channel, wherein the mutant light-inducible ion channel comprises an amino acid sequence which has at least 90% similarity/homology and/or at least 72% identity to the full length sequence of SEQ ID NO: 1 (Chrimson), and wherein the mutant light-inducible ion channel only differs from its parent light-inducible ion channel by a substitution at one or more position(s) selected from the positions corresponding to Y261, Y268, and S267 in SEQ ID NO: 1, which substitution(s) accelerate(s) the off-kinetics of the mutant channel as compared to the parent channel, when compared by patch-clamp measurements in the whole cell configuration at a clamp potential of −60 mV, a bath solution of 140 mM NaCl, 2 mM $CaCl_2$, 2 $MgCl_2$, 10 mM HEPES, pH 7.4, and a pipette solution of 110 mM NaCl, 2 mM $MgCl_2$, 10 mM EGTA, 10 mM HEPES, pH 7.4. The off-kinetics of the mutant and the parent channel can be measured in rat hippocampal cells (see Example 3 below), or in NG108-15 neuroblastoma cells (see Example 1 below), each heterologously expressing the mutant or parent channel. Preferably, the off-kinetics of the mutant channel are measured in NG108-15 cells. Successful protein expression can be proven, for example, by EGFP- or YFP-mediated fluorescence. Generally, photocurrents are measured in response 3 ms light pulses with an intensity of 23 mW/mm$^2$ and a wavelength of 594 nm. The $T_{off}$ value is determined by a fit of the current after cessation of illumination to a monoexponential function, as further described in the examples below.

In a preferred embodiment, the mutant light-inducible ion channel comprises a substitution at position Y261. In a particularly preferred embodiment, the substitution is Y261F.

Alternatively, or in addition to the substitution at position Y261, the mutant light-inducible ion channel comprises a substitution at position Y268. More preferably, the substitution is Y268F.

In still another preferred embodiment, the mutant light-inducible ion channel comprises a substitution at position S267. In a particularly preferred embodiment, the substitution is S267M. Even more preferably, said substitution is combined with the substitution at position Y261, at position Y268, or both at positions Y261 and Y268.

Hence, in a preferred embodiment, the mutant light-inducible ion channel comprises a substitution at position Y261 and at position S267, preferably wherein the substitution at position Y261 is Y261F, and preferably wherein the substitution at position S267 is S267M. In another preferred embodiment, the mutant light-inducible ion channel comprises a substitution at position Y268 and at position S267, preferably wherein the substitution at position Y268 is Y268F, and preferably wherein the substitution at position S267 is S267M. In still another preferred embodiment the mutant light-inducible ion channel comprises a substitution at position Y261, at position Y268, and at position S267, preferably wherein the substitution at position Y261 is Y261F, preferably wherein the substitution at position Y268 is Y268F, and preferably wherein the substitution at position S267 is S267M.

The parent light-inducible ion channel may be any Chrimson-like channel, as long as it falls within the required percentage sequence identity and/or sequence homology/similarity. In one preferred embodiment, the parent light-inducible ion channel already comprises an Arg at the position corresponding to position 176 of SEQ ID NO: 1. Said variant is already known as ChrimsonR (K176R).

Preferably, the mutant light-inducible ion channel has at least 91%, preferably at least 92%, more preferably at least 93%, more preferably at least 94%, more preferably at least 95%, more preferably at least 96%, more preferably at least 97%, more preferably at least 98%, more preferably at least 99% similarity/homology to the full length of SEQ ID NO: 1 (Chrimson).

In addition, or alternatively, the mutant light-inducible ion channel has at least 74%, preferably at least 75%, more preferably at least 76%, more preferably at least 78%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identity to the full length of SEQ ID NO: 1 (Chrimson).

Examples of light-inducible ion channels, which have at least 70% similarity/homology or at least 70% identity to the full length of SEQ ID NO: 1 are the ChrimsonR variant K176R, or the chimera CsChrimson (SEQ ID NO: 2, accession number KJ995863), and any other ortholog or allelic variant thereof. Chrimson and CsChrimson share 74% identity and 76.4% homology/similarity over the full length of Chrimson (SEQ ID NO: 1).

Preferably, the mutant light-inducible ion channel is a red light absorbing channelrhodopsin.

Also contemplated are swap mutants of a light-inducible ion channel, in which helix 6 has been replaced by the helix-6 motif of SEQ ID NO: 3, e.g. ChR-2 (SEQ ID NO: 5), VChR1 (SEQ ID NO: 6), or ReaChR (SEQ ID NO: 7) in which helix 6 is replaced by helix 6 of Chrimson including the Y268F, Y261F, and S267M substitutions, respectively (cf. SEQ ID NO: 8, 9, and 10).

Such a swap mutant has typically at least 56% homology/similarity to the full length of SEQ ID NO: 1 (Chrimson), preferably at least 58%, more preferably at least 60%, more preferably at least 62%, and even more preferably at least 64% homology/similarity to the full length of SEQ ID NO: 1 (Chrimson).

In addition, or alternatively, such a swap mutant has typically at least 42%, preferably at least 44%, more preferably at least 46%, more preferably at least 48%, more preferably at least 50%, more preferably at least 52%, more preferably at least 54%, more preferably at least 56% identity to the full length of SEQ ID NO: 1 (Chrimson).

Generally, an amino acid sequence has "at least x %" identity" with another amino acid sequence, e.g. SEQ ID NO: 1 above, when the sequence identity between those to aligned sequences is at least x % over the full length of said other amino acid sequence, e.g. SEQ ID NO: 1. Similarly, an amino acid sequence has "at least x % similarity/homology" with another amino acid sequence, e.g. SEQ ID NO: 1 above, when the sequence similarity/homology between those to aligned sequences is at least x % over the full length of said other amino acid sequence, e.g. SEQ ID NO: 1.

Such alignments can be performed using for example publicly available computer homology programs such as the "EMBOSS" program provided at the EMBL homepage (available on the World Wide Web at ebi.ac.uk/Tools/psa/emboss_needle/) using the default settings provided therein. Further methods of calculating sequence identity or sequence similarity/homology percentages of sets of amino acid sequences are known in the art.

However, in a particularly preferred embodiment, the mutant light-inducible ion channel comprises, more preferably consists of the amino acid sequence of SEQ ID NO: 1 (Chrimson), except for said substitution(s) at position Y261, Y268, and 5267, and optionally the Arg at the position corresponding to position 176 of SEQ ID NO: 1, as further disclosed above.

The light inducible ion channel of the present disclosure is a membrane protein with at least 5 transmembrane helices, which is capable of binding a light-sensitive polyene. Transmembrane proteins with 6 or 7 transmembrane helices are preferable. Transmembrane proteins with more than 7 helices, for example 8, 9 or 10 transmembrane helices, are however also encompassed. Furthermore, the invention covers transmembrane proteins which in addition to the transmembrane part include C- and/or N-terminal sequences, where the C-terminal sequences can extend into the inside of the lumen enclosed by the membrane, for example the cytoplasm of a cell or the inside of a liposome, or can also be arranged on the membrane outer surface. The same applies for the optionally present N-terminal sequences, which can likewise be arranged both within the lumen and also on the outer surface of the membrane. The length of the C- and/or N-terminal sequences is in principle subject to no restriction; however, light-inducible ion channels with C-terminal sequences not embedded in the membrane, with 1 to 1000 amino acids, preferably 1 to 500, especially preferably 5 to 50 amino acids, are preferred. Independently of the length of the C-terminal sequences, the N-terminal located sequences not embedded in the membrane preferably comprise 1 to 500 amino acids, especially preferably 5 to 50 amino acids. The concept of the transmembrane helix is well known to the skilled person. These are generally α-helical protein structures, which as a rule comprise 20 to 25 amino acids. However, depending on the nature of the membrane, which can be a natural membrane, for example a cell or plasma membrane, or also a synthetic membrane, the transmembrane segments can also be shorter or longer. For example, transmembrane segments in artificial membranes can comprise up to 30 amino acids, but on the other hand also only a few amino acids, for example 12 to 16.

In addition, the light-inducible ion channel comprises further (semi-)conservative substitutions as compared to SEQ ID NO: 1. Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc. Typical semi-conservative and conservative substitutions are:

| Amino acid | Conservative substitution | Semi-conservative substitution |
|---|---|---|
| A | G; S; T | N; V; C |
| C | A; V; L | M; I; F; G |
| D | E; N; Q | A; S; T; K; R; H |
| E | D; Q; N | A; S; T; K; R; H |
| F | W; Y; L; M; H | I; V; A |
| G | A | S; N; T; D; E; N; Q |
| H | Y; F; K; R | L; M; A |
| I | V; L; M; A | F; Y; W; G |
| K | R; H | D; E; N; Q; S; T; A |
| L | M; I; V; A | F; Y; W; H; C |
| M | L; I; V; A | F; Y; W; C; |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |
| V | A; L; I | M; T; C; N |
| W | F; Y; H | L; M; I; V; C |
| Y | F; W; H | L; M; I; V; C |

Furthermore, the skilled person will appreciate that glycines at sterically demanding positions should not be substituted and that proline should not be introduced into parts of the protein which have an alpha-helical or a beta-sheet structure.

Preferably, the mutant channel comprises the helix 6-motif of SEQ ID NO: 3:

Cys-Arg-Met-Val-Val-Lys-Leu-Met-Ala-Tyr-Ala-$Xaa_{12}$-Phe-Ala-Ser-Trp-Gly-$Xaa_{18}$-$Xaa_{19}$-Pro-Ile-Leu-Trp-Ala-Val, wherein $Xaa_{12}$ is Phe or Tyr, preferably wherein $Xaa_{12}$ is Phe;

wherein $Xaa_{18}$ is Met or Ser, preferably wherein $Xaa_{18}$ is Met; and wherein $Xaa_{19}$ is Tyr or Phe, preferably wherein $Xaa_{19}$ is Phe.

It is further preferred that the light-inducible ion channel comprises the consensus motif L(I,A,C)DxxxKxxW(F,Y) (SEQ ID NO: 4). Amino acids given in brackets can in each case replace the preceding amino acid. This consensus sequence is the motif surrounding the retinal-binding amino acid lysine.

In general, the retinal or retinal derivative necessary for the functioning of the light-inducible ion channel is produced by the cell to be transfected with said ion channel. Depending on its conformation, the retinal may be all-trans retinal, 11-cis-retinal, 13-cis-retinal, or 9-cis-retinal. However, it is also contemplated that the mutant light-inducible ion channel of the invention may be incorporated into vesicles, liposomes or other artificial cell membranes. Accordingly, also disclosed is a channelrhodopsin, comprising the light-inducible ion channel of the present disclosure, and a retinal or retinal derivative. Preferably, the retinal derivative is selected from the group consisting of 3,4-dehydroretinal, 13-ethylretinal, 9-dm-retinal, 3-hydroxyretinal, 4-hydroxyretinal, naphthylretinal; 3,7,11-trimethyl-dodeca-2,4,6,8, 10-pentaenal; 3,7-dimethyl-deca-2,4,6,8-tetraenal; 3,7-dimethyl-octa-2,4,6-trienal; and 6-7 rotation-blocked retinals, 8-9 rotation-blocked retinals, and 10-11 rotation-blocked retinals.

The present disclosure also describes a nucleic acid construct, comprising a nucleotide sequence coding for the mutant light-inducible ion channel as disclosed herein above.

To ensure optimal expression, the coding DNA can also be suitably modified, for example by adding suitable regulatory sequences and/or targeting sequences and/or by matching of the coding DNA sequence to the preferred codon usage of the chosen host. The targeting sequence may encode a C-terminal extension targeting the light-inducible ion channel to a particular site or compartment within the cell, such as to the synapse or to a post-synaptic site, to the axon-hillock, or the endoplasmic reticulum. The nucleic acid may be combined with further elements, e.g., a promoter and a transcription start and stop signal and a translation start and stop signal and a polyadenylation signal in order to provide for expression of the sequence of the mutant light-inducible ion channel of the present disclosure. The promoter can be inducible or constitutive, general or cell specific promoter. An example of a cell-specific promoter is the mGlu6-promotor specific for bipolar cells. Selection of promoters, vectors and other elements is a matter of routine design within the level of ordinary skill in the art. Many such elements are described in the literature and are available through commercial suppliers.

Also disclosed is an expression vector, comprising a nucleotide sequence coding for the mutant light-inducible ion channel or the nucleic acid construct as disclosed herein. In a preferred embodiment, the vector is suitable for gene therapy, in particular wherein the vector is suitable for virus-mediated gene transfer. The term "suitable for virus-mediated gene transfer" means herein that said vector can be packed in a virus and thus be delivered to the site or the cells of interest. Examples of viruses suitable for gene therapy are retroviruses, adenoviruses, adeno-associated viruses, lentiviruses, pox viruses, alphaviruses, rabies virus, semliki forest virus and herpes viruses. These viruses differ in how well they transfer genes to the cells they recognize and are able to infect, and whether they alter the cell's DNA permanently or temporarily. However, gene therapy also encompasses non-viral methods, such as application of naked DNA, lipoplexes and polyplexes, and dendrimers.

As described above, the resulting nucleic acid sequence may be introduced into cells e.g. using a virus as a carrier or by transfection including e.g. by chemical transfectants (such as Lipofectamine, Fugene, etc.), electroporation, calcium phosphate co-precipitation and direct diffusion of DNA. A method for transfecting a cell is detailed in the examples and may be adapted to the respective recipient cell. Transfection with DNA yields stable cells or cell lines, if the transfected DNA is integrated into the genome, or unstable (transient) cells or cell lines, wherein the transfected DNA exists in an extrachromosomal form. Furthermore, stable cell lines can be obtained by using episomal replicating plasmids, which means that the inheritance of the extrachromosomal plasmid is controlled by control elements that are integrated into the cell genome. In general, the selection of a suitable vector or plasmid depends on the intended host cell.

Therefore, the present disclosure also pertains to a cell comprising the nucleic acid construct or the expression vector as disclosed herein.

The incorporation of the mutant light-inducible ion channel into the membrane of cells which do not express the corresponding channels in nature can for example be simply effected in that, using known procedures of recombinant DNA technology, the DNA coding for this ion channel is firstly incorporated into a suitable expression vector, e.g. a plasmid, a cosmid or a virus, the target cells are then transformed with this, and the protein is expressed in this host. Next, the cells are treated in a suitable manner, e.g. with retinal, in order to enable the linkage of a Schiffs base between protein and retinal.

The expression of the light-inducible ion channel of the present disclosure can be advantageously effected in certain mammalian cell systems. Thus, in a preferred embodiment, the cell is a mammalian cell. The expression is effected either with episomal vectors as transient expression, preferably in neuroblastoma cells (e.g., NG108-15-Cells), melanoma cells (e.g., the BLM cell line), COS cells (generated by infection of "African green monkey kidney CV1" cells) or HEK cells ("human embryonic kidney cells", e.g. HEK293 cells), or BHK-cells ("baby hamster kidney cells"), or in the form of stable expression (by integration into the genome) in CHO cells ("Chinese hamster ovary cells"), myeloma cells or MDCK cells ("Madine-Darby canine kidney cells") or in Sf9 insect cells infected with baculoviruses. Accordingly, in a more preferred embodiment the mammalian cell is a COS cell; a BHK cell; a HEK293 cell; a CHO cell; a myeloma cell; or a MDCK cell.

In a preferred embodiment, the mammalian cell is an electrically excitable cell. It is further preferred that the cell is a hippocampal cell, a photoreceptor cell; a retinal rod cell; a retinal cone cell; a retinal ganglion cell; a bipolar neuron; a ganglion cell; a pseudounipolar neuron; a multipolar neuron; a pyramidal neuron, a Purkinje cell; or a granule cell.

A neuron is an electrically excitable cell that processes and transmits information by electrical and chemical signalling, wherein chemical signalling occurs via synapses, specialized connections with other cells. A number of specialized types of neurons exist such as sensory neurons responding to touch, sound, light and numerous other stimuli affecting cells of the sensory organs, motor neurons receiving signals from the brain and spinal cord and causing muscle contractions and affecting glands, and interneurons connecting neurons to other neurons within the same region of the brain or spinal cord. Generally, a neuron possesses a soma, dendrites, and an axon. Dendrites are filaments that arise from the cell body, often extending for hundreds of microns and branching multiple times. An axon is a special cellular filament that arises from the cell body at a site called the axon hillock. The cell body of a neuron frequently gives rise to multiple dendrites, but never to more than one axon, although the axon may branch hundreds of times before it terminates. At the majority of synapses, signals are sent from the axon of one neuron to a dendrite of another. There are, however, many exceptions to these rules: neurons that lack dendrites, neurons that have no axon, synapses that connect an axon to another axon or a dendrite to another dendrite, etc. Most neurons can further be anatomically characterized as unipolar or pseudounipolar (dendrite and axon emerge from same process), bipolar (axon and single dendrite on opposite ends of the soma), multipolar (having more than two dendrites and may be further classified as (i) Golgi I neurons with long-projecting axonal processes, such as pyramidal cells, Purkinje cells, and anterior horn cells, and (ii) Golgi II: neurons whose axonal process projects locally, e.g., granule cells.

A photoreceptor cell, is a specialized neuron found in the retina that is capable of phototransduction. The two classic photoreceptors are rods and cones, each contributing information used by the visual system. A retinal ganglion cell is a type of neuron located near the inner surface of the retina of the eye. These cells have dendrites and long axons projecting to the protectum (midbrain), the suprachiasmatic nucleus in the hypothalamus, and the lateral geniculate (thalamus). A small percentage contribute little or nothing to vision, but are themselves photosensitive. Their axons form the retinohypothalamic tract and contribute to circadian rhythms and pupillary light reflex, the resizing of the pupil. They receive visual information from photoreceptors via two intermediate neuron types: bipolar cells and amacrine cells. Amacrine cells are interneurons in the retina, and responsible for 70% of input to retinal ganglion cells. Bipolar cells, which are responsible for the other 30% of input to retinal ganglia, are regulated by amacrine cells. As a part of the retina, the bipolar cell exists between photoreceptors (rod cells and cone cells) and ganglion cells. They act, directly or indirectly, to transmit signals from the photoreceptors to the ganglion cells.

The cell may be isolated (and genetically modified), maintained and cultured at an appropriate temperature and gas mixture (typically, 37° C., 5% $CO_2$), optionally in a cell incubator as known to the skilled person and as exemplified for certain cell lines or cell types in the examples. Culture conditions may vary for each cell type, and variation of conditions for a particular cell type can result in different phenotypes. Aside from temperature and gas mixture, the most commonly varied factor in cell culture systems is the growth medium. Recipes for growth media can vary in pH, glucose concentration, growth factor and the presence of other nutrient components among others. Growth media are either commercially available, or can be prepared according to compositions, which are obtainable from the American Tissue Culture Collection (ATCC). Growth factors used for supplement media are often derived from animal blood such as calf serum. Additionally, antibiotics may be added to the growth media. Amongst the common manipulations carried out on culture cells are media changes and passaging cells. The present disclosure further pertains to a use of a mutant light-inducible ion channel, or a cell according to the present disclosure in a high-throughput screening. A high-throughput screening (HTS), is a method for scientific experimentation especially used in drug discovery and relevant to the fields of biology and chemistry. HTS allows a researcher to effectively conduct millions of biochemical, genetic or pharmacological tests in a short period of time, often through a combination of modern robotics, data processing and control software, liquid handling devices, and sensitive detectors. By this process, one may rapidly identify active agents which modulate a particular biomolecular pathway; particularly a substance modifying an ion channel, such as the light-inducible ion channel according to the invention, a $Ca^{++}$-inducible potassium channel, or a BK channel. For example, one might co-express the $Ca^{++}$-inducible potassium channel and the light-inducible ion channel in a host cell. Upon stimulation by light, the light-inducible channel will open and the intracellular $Ca^{++}$ concentration will increase, thereby activating the potassium channel. Thus, one will receive a change in the membrane potential, which may be monitored by potential-sensitive dyes such as RH 421 (N-(4-Sulfobutyl)-4-(4-(4-(dipentylamino)phenyl)butadienyl)pyridinium, inner salt). Such a HTS may thus comprise the following steps: (i) contacting a cell expressing a $Ca^{++}$-inducible (potassium) channel and the light-inducible ion channel according to the invention with a candidate agent directed against the $Ca^{++}$-inducible channel, (ii) applying a light stimulus in order to induce the light-inducible channel, (iii) determining the alteration of the membrane potential (mixed signal), and (iv) comparing the signal determined in step (iii) with the signal determined in a cell only expressing the light-inducible ion channel according to the invention subjected to step (ii) (single signal). A reduction in the change of the membrane potential would be indicative of a promising modulator of the $Ca^{++}$-inducible (potassium) channel. Such an approach is supposed to yield a signal-to-noise ratio of approximately 5:1, which is quite improved compared to direct measurements conducted on a cell only expressing the $Ca^{++}$-inducible channel. Due to the improved signal-to-noise ratio, said method, in particular by using the light-inducible ion channel, may be particularly suitable for HTS.

In essence, HTS uses an approach to collect a large amount of experimental data on the effect of a multitude of substances on a particular target in a relatively short time. A screen, in this context, is the larger experiment, with a single goal (usually testing a scientific hypothesis), to which all this data may subsequently be applied. For HTS cells according to the invention may be seed in a tissue plate, such as a multi well plate, e.g. a 96-well plate. Then the cell in the plate is contacted with the test substance for a time sufficient to interact with the targeted ion channel. The test substance may be different from well to well across the plate. After incubation time has passed, measurements are taken across all the plate's wells, either manually or by a machine and optionally compared to measurements of a cell which has not been contacted with the test substance. Manual measurements may be necessary when the researcher is using patch-clamp, looking for effects not yet implemented in automated routines. Otherwise, a specialized automated analysis machine can run a number of experiments on the wells (such as analysing light of a particular frequency or a high-throughput patch-clamp measurement). In this case, the machine outputs the result of each experiment e.g. as a grid of numeric values, with each number mapping to the value obtained from a single well. Depending upon the results of this first assay, the researcher can perform follow up assays within the same screen by using substances similar to those identified as active (i.e. modifying an intracellular cyclic nucleotide level) into new assay plates, and then re-running the experiment to collect further data, optimize the structure of the chemical agent to improve the effect of the agent on the cell. Automation is an important element in HTS's usefulness. A specialized robot is often responsible for much of the process over the lifetime of a single assay plate, from creation through final analysis. An HTS robot can usually prepare and analyze many plates simultaneously, further speeding the data-collection process. Examples for apparatuses suitable for HTS in accordance with the present invention comprise a Fluorometric Imaging Plate Reader (FLIPR™; Molecular Devices), FLEXstation™ (Molecular Devices), Voltage Ion Probe Reader (VIPR, Aurora Biosciences), Attofluor® Ratio Vision® (ATTO).

Thus, the presently disclosed mutant light-inducible ion channel is particularly useful as a research tool, such as in a non-therapeutic use for light-stimulation of electrically excitable cells, in particular neuron cells. Further guidance, e.g., with regard to Hippocampal neuron culture, and electrophysiological recordings from hippocampal neurons, as well as electrophysiological recordings on HEK293 cells, can be found in WO 2012/032103.

Finally, there are a number of diseases in which, e.g., the natural visual cells no longer function, but all nerve connections are capable of continuing to operate. Today, attempts are being made in various research centres to implant thin films with artificial ceramic photocells on the retina. These photocells are intended to depolarise the secondary, still intact cells of the retinal and thereby to trigger a nerve impulse (bionic eyes). The deliberate expression of mutant light-controlled ion channels according to the present disclosure in these ganglion cells, amacrine cells or bipolar cells would be a very much more elegant solution and enable greater three-dimensional visual resolution. Therefore, the present disclosure also contemplates the light-inducible ion channel according to the present disclosure for use in medicine.

The proof of principle is already demonstrated in the examples below, and can easily be adapted to the respective purpose. In view of these data, it is contemplated that the presently disclosed light-inducible ion channels can be used for restoring auditory activity in deaf subjects, or recovery of vision in blind subjects. More specifically, as demonstrated in the examples below, the mutant light-inducible ion channels of the present disclosure provide sufficient temporal fidelity. Their red-shifted spectrum is advantageous for deeper light penetration and less scattering in the tissue as well as less risk of phototoxicity. Therefore, it is anticipated that the presently disclosed mutant light-inducible ion channels will become a valuable tool for optogenetic hearing restoration and auditory research. In still another embodiment, it is contemplated that the presently disclosed light-inducible ion channels can be used in afferent feedback for improving sensory-motor prosthetic of limbs, such as an arm or a leg. Afferent feedback refers to nerve signals sent from the peripheral nerves of the body to the brain or spinal cord. It is further contemplated that the presently disclosed light-inducible ion channels can be used in the treatment of pain, in particular phantom limb pain, or chronic pain.

Further described are non-human animals which functionally express the light-inducible ion channel according to the present disclosure, e.g. in an electrically excitable cell such as a neuron, in particular in spiral ganglion neurons, as also described for the cell of the present disclosure. Likewise, also contemplated are non-human animals, which comprise a cell according to the present disclosure.

The non-human animal may be any animal other than a human. In a preferred embodiment, the non-human animal is a vertebrate, preferably a mammal, more preferably a rodent, such as a mouse or a rat, or a primate.

In particular, some model organisms are preferred, such as *Caenorhabditis elegans, Arbacia punctulata, Ciona intestinalis, Drosophila*, usually the species *Drosophila melanogaster, Euprymna scolopes, Hydra, Loligo pealei, Pristionchus pacificus, Strongylocentrotus purpuratus, Symsagittifera roscoffensis*, and *Tribolium castaneum*. Among vertebrates, these are several rodent species such as guinea pig (*Cavia porcellus*), hamster, mouse (*Mus musculus*), and rat (*Rattus norvegicus*), as well as other species such as chicken (*Gallus gallus domesticus*), cat (*Felis cattus*), dog (*Canis lupus familiaris*), Lamprey, Japanese ricefish (*Oryzias latipes*), Rhesus macaque, *Sigmodon hispidus*, zebra finch (*Taeniopygia guttata*), pufferfish (*Takifugu rubripres*), african clawed frog (*Xenopus laevis*), and zebrafish (*Danio rerio*). Also preferred are non-human primates, i.e. all species of animals under the order Primates that are not a member of the genus Homo, for example rhesus macaque, chimpanzee, baboon, marmoset, and green monkey. However, these examples are not intended to limit the scope of the invention.

It is noted that those animals are excluded, which are not likely to yield in substantial medical benefit to man or animal and which are therefore not subject to patentability under the respective patent law or jurisdiction. Moreover, the skilled person will take appropriate measures, as e.g. laid down in international guidelines of animal welfare, to ensure that the substantial medical benefit to man or animal will outweigh any animal suffering.

In the following, the present invention is illustrated by figures and examples which are not intended to limit the scope of the present invention.

DESCRIPTION OF THE SEQUENCES

Figure 1:
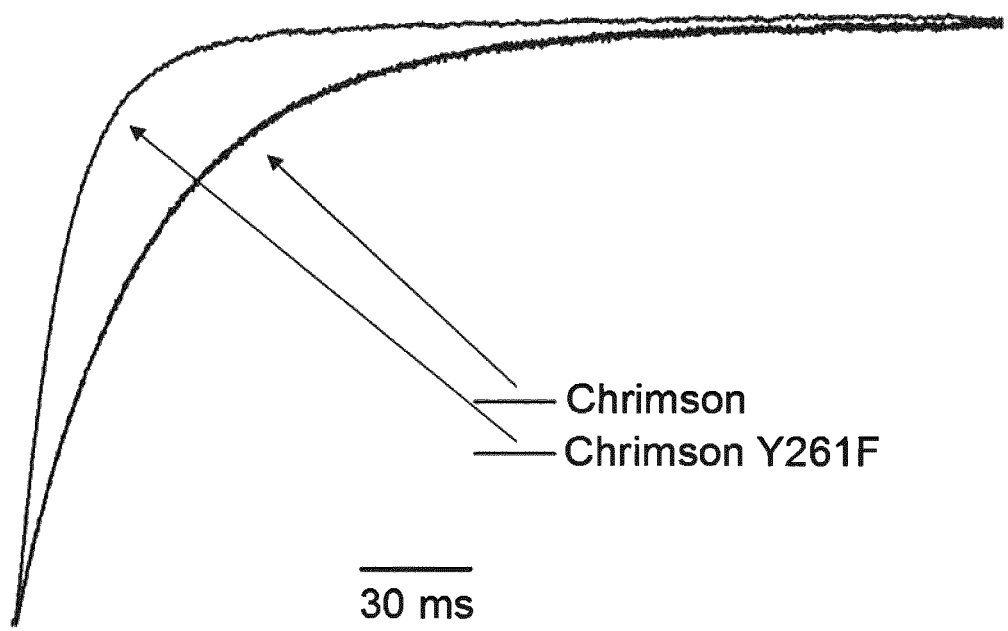
FIG. 1: Off-kinetics of Chrimson and Chrimson Y261F. Shown are typical photo currents of Chrimson-YFP and Chrimson-YFP Y261F immediately after cessation of illumination. The currents were normalized for comparison.

SEQ ID NO: 1 Chrimson; accession number KF992060; helix 6 highlighted in bold)
MAELISSATRSLFAAGGINPWPNPYHHEDMGCGGMTPTGECFSTEWWCDPSY
GLSDAGYGYCFVEATGGYLVVGVEKKQAWLHSRGTPGEKIGAQVCQWIAFSIAI
ALLTFYGFSAWKATCGWEEVYVCCVEVLFVTLEIFKEFSSPATVYLSTGNHAYCL
RYFEWLLSCPVILIKLSNLSGLKNDYSKRTMGLIVSCVGMIVFGMAAGLATDWLK

| DESCRIPTION OF THE SEQUENCES |
|---|

WLLYIVSCIYGGYMYFQAAKCYVEANHSVPKGH**CRMVVKLMAYAYFASWGSYP
ILWAV**GPEGLLKLSPYANSIGHSICDIIAKEFWTFLAHHLRIKIHEHILIHGDIRKTTK
EIGGEEVEVEEFVEEEDEDTV

SEQ ID NO: 2 (CsChrimson; accession number KJ995863; helix 6
highlighted in bold)
MSRLVAASWLLALLLCGITSTTTASSAPAASSTDGTAAAAVSHYAMNGFDELAKG
AVVPEDHFVCGPADKCYCSAWLHSRGTPGEKIGAQVCQWIAFSIAIALLTFYGFS
AWKATCGWEEVYVCCVEVLFVTLEIFKEFSSPATVYLSTGNHAYCLRYFEWLLS
CPVILIKLSNLSGLKNDYSKRTMGLIVSCVGMIVFGMAAGLATDWLKWLLYIVSCIY
GGYMYFQAAKCYVEANHSVPKGHCRMWKLMAYAYFASWGSYPILWAVGPEG
LLKLSPYANSIGHSICDIIAKEFWTFLAHHLRIKIHEHILIHGDIRKTTKMEIGGEEVE
VEEFVEEEDEDTV SEQ ID NO: 3 (Helix 6 Consensus Motif)
Cys-Arg-Met-Val-Val-Lys-Leu-Met-Ala-Tyr-Ala-Xaa$_{12}$-Phe-
Ala-Ser-Trp-Gly-Xaa$_{18}$-Xaa$_{19}$-Pro-Ile-Leu-Trp-Ala-Val,
wherein Xaa$_{12}$ is Phe or Tyr, preferably wherein Xaa$_{12}$ is Phe;
wherein Xaa$_{18}$ is Met or Ser, preferably wherein Xaa$_{18}$ is Met; and
wherein Xaa$_{19}$ is Phe or Tyr, preferably wherein Xaa$_{19}$ is Phe.

SEQ ID NO: 4 (Retinal binding site consensus motif)
Xaa$_1$-Asp-Xaa$_3$-Xaa$_4$-Xaa$_5$-Lys-Xaa$_7$-Xaa$_8$-Xaa$_9$
wherein Xaa$_1$ is Leu, Ile, Ala, or Cys;
wherein Xaa$_3$, Xaa$_4$, Xaa$_5$, Xaa$_7$, and Xaa$_8$ is independently any amino acid;
wherein Xaa$_9$ is Thr, Phe, or Tyr.

SEQ ID NO: 5 (Channelrhodopsin 2; ChR2; 315 aa; helix 6 highlighted
in bold)
MDYGGALSAVGRELLFVTNPVVVNGSVLVPEDQCYCAGWIESRGTNGAQTASN
VLQWLAAGFSILLLMFYAYQTWKSTCGWEEIYVCAIEMVKVILEFFFEFKNPSMLY
LATGHRVQWLRYAEWLLTCPVILIHLSNLTGLSNDYSRRTMGLLVSDIGTIVWGA
TSAMATGYVKVIFFCLGLCYGANTFFHAAKAYIEGYHTVPKGR**CRQVVTGMAWL
FFVSWGMFPILFIL**GPEGFGVLSVYGSTVGHTIIDLMSKNCWGLLGHYLRVLIHEH
ILIHGDIRKTTKLNIGGTEIEVETLVEDEAEAGAVNKGTGK SEQ ID NO: 6 (VChR1; accession number EU622855; 300 aa; helix 6
highlighted in bold)
MDYPVARSLIVRYPTDLGNGTVCMPRGQCYCEGWLRSRGTSIEKTIAITLQWVV
FALSVACLGWYAYQAWRATCGWEEVYVALIEMMKSIIEAFHEFDSPATLWLSSG
NGVVWMRYGEWLLTCPVLLIHLSNLTGLKDDYSKRTMGLLVSDVGCIVWGATSA
MCTGWTKILFFLISLSYGMYTYFHAAKVYIEAFHTVPKGI**CRELVRVMAWTFFVA
WGMFPVLFLL**GTEGFGHISPYGSAIGHSILDLIAKNMWGVLGNYLRVKIHEHILLY
GDIRKKQKITIAGQEMEVETLVAEEED SEQ ID NO: 7 (ReaChR; accession number KF448069; 352 aa; helix 6
highlighted in bold)
MVSRRPWLLALALAVALAAGSAGASTGSDATVPVATQDGPDYVFHRAHERMLF
QTSYTLENNGSVICIPNNGQCFCLAWLKSNGTNAEKLAANILQWVVFALSVACLG
WYAYQAWRATCGWEEVYVALIEMMKSIIEAFHEFDSPATLWLSSGNGVVWMRY
GEWLLTCPVILIHLSNLTGLKDDYSKRTMGLLVSDVGCIVWGATSAMCTGWTKIL
FFLISLSYGMYTYFHAAKVYIEAFHTVPKGL**CRQLVRAMAWLFFVSWGMFPVLF
LL**GPEGFGHISPYGSAIGHSILDLIAKNMWGVLGNYLRVKIHEHILLYGDIRKKQKI
TIAGQEMEVETLVAEEEDKYESSLE SEQ ID NO: 8 (ChR2; Helix 6 swap mutant)
MDYGGALSAVGRELLFVTNPVVVNGSVLVPEDQCYCAGWIESRGTNGAQTASN
VLQWLAAGFSILLLMFYAYQTWKSTCGWEEIYVCAIEMVKVILEFFFEFKNPSMLY
LATGHRVQWLRYAEWLLTCPVILIHLSNLTGLSNDYSRRTMGLLVSDIGTIVWGA
TSAMATGYVKVIFFCLGLCYGANTFFHAAKAYIEGYHTVPKGR**CRMVVKLMAYA
YFASWGSYPILWAV**GPEGFGVLSVYGSTVGHTIIDLMSKNCWGLLGHYLRVLIHE
HILIHGDIRKTTKLNIGGTEIEVETLVEDEAEAGAVNKGTGK SEQ ID NO: 9 (VChR1 Helix 6 swap mutant)
MDYPVARSLIVRYPTDLGNGTVCMPRGQCYCEGWLRSRGTSIEKTIAITLQWVV
FALSVACLGWYAYQAWRATCGWEEVYVALIEMMKSIlEAFHEFDSPATLWLSSG
NGVVWMRYGEWLLTCPVLLIHLSNLTGLKDDYSKRTMGLLVSDVGCIVWGATSA
MCTGWTKILFFLISLSYGMYTYFHAAKVYIEAFHTVPKGI**CRMWKLMAYAYFAS
WGSYPILWAV**GTEGFGHISPYGSAIGHSILDLIAKNMWGVLGNYLRVKIHEHILLY
GDIRKKQKITIAGQEMEVETLVAEEED SEQ ID NO: 10 (ReaChR; Helix 6 swap mutant)
MVSRRPWLLALALAVALAAGSAGASTGSDATVPVATQDGPDYVFHRAHERMLF
QTSYTLENNGSVICIPNNGQCFCLAWLKSNGTNAEKLAANILQWVVFALSVACLG
WYAYQAWRATCGWEEVYVALIEMMKSIIEAFHEFDSPATLWLSSGNGVVWMRY
GEWLLTCPVILIHLSNLTGLKDDYSKRTMGLLVSDVGCIVWGATSAMCTGWTKIL -continued

DESCRIPTION OF THE SEQUENCES

FFLISLSYGMYTYFHAAKVYIEAFHTVPKGLCRMVVKLMAYAYFASWGSYPILWA
VGPEGFGHISPYGSAIGHSILDLIAKNMWGVLGNYLRVKIHEHILLYGDIRKKQKITI
AGQEMEVETLVAEEEDKYESSLE

EXAMPLE

The inventors' objective was to identify residues within the sixth transmembrane domain of Chrimson whose mutations are capable of accelerating the off-kinetics.

Example 1—Photocurrents of Chrimson Mutants in NG108-15 Cells

NG108-15 cells transiently expressing Chrimson-YFP and Chrimson-YFP mutants were investigated by patch-clamp measurements in the whole cell configuration at a clamped potential of −60 mV. The bath solution contained 140 mM NaCl, 2 mM $CaCl_2$, 2 mM $MgCl_2$, 10 mM HEPES, pH 7.4 and the pipette solution contained 110 mM NaCl, 2 mM $MgCl_2$, 10 mM EGTA, 10 mM HEPES, pH 7.4. Photocurrents were measured in response to 3 ms light pulses with an intensity of 23 $mW/mm^2$, and a wavelength of 594 nm. The $T_{off}$ value was determined by a fit of the currents after cessation of illumination to a monoexponential function. The current density ($J_{-60\ mV}$) was determined by dividing the stationary current in response to a 500 ms light pulse with an intensity of 23 $mW/mm^2$, and a wavelength of 594 nm by the capacitance of the cell.

Figure 2:
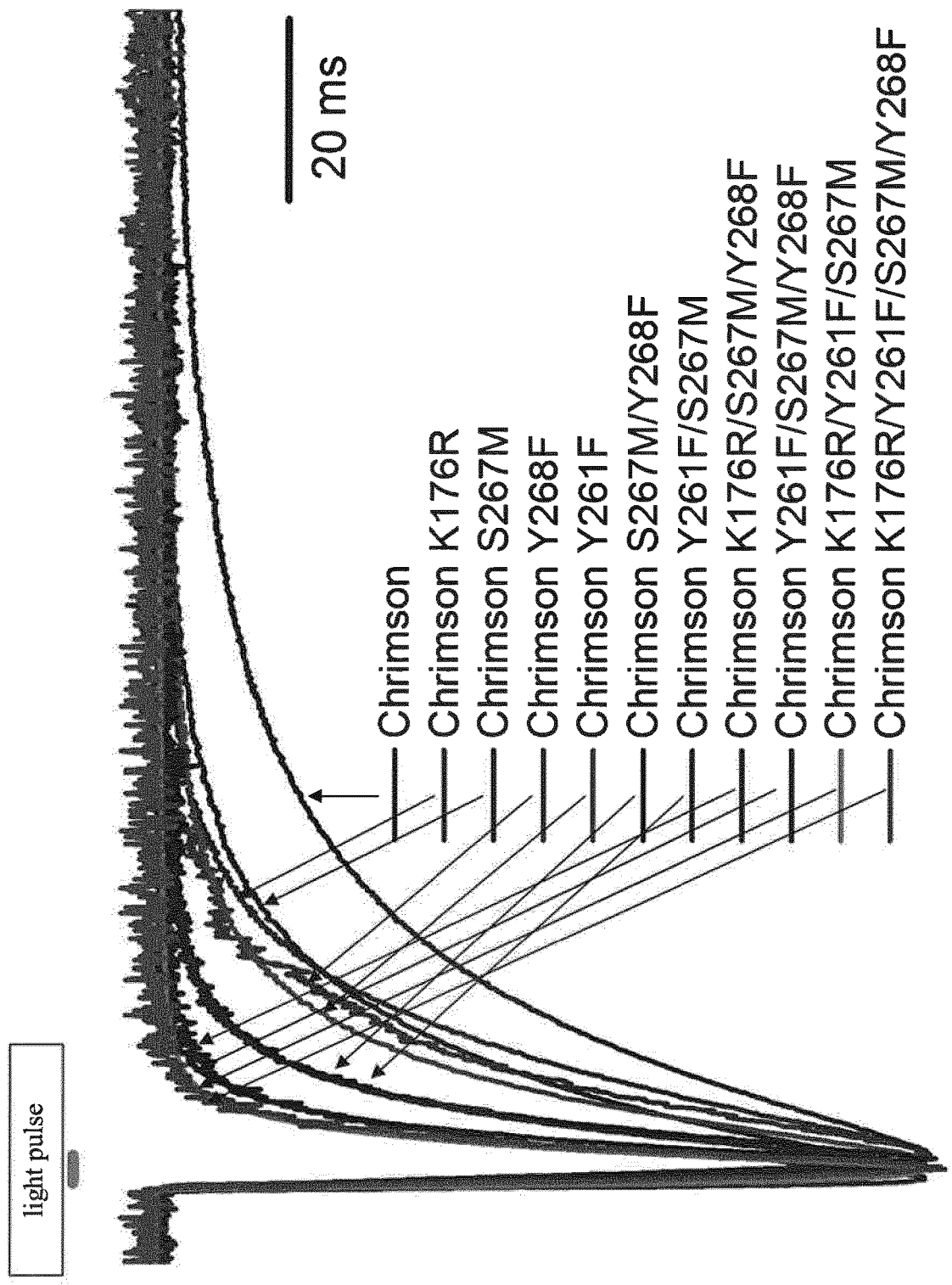
FIG. 2: Photocurrents of Chrimson and Chrimson mutants. Shown are typical photocurrents which were measured in response to 3 ms light-pulses with a wavelength of 594 nm and a saturating light intensity of 23 mW/mm$^{-2}$. NG108-15 cells which were heterologously expressing Chrimson-YFP ( ———— ), Chrimson-YFP K176R ( ———— ) Chrimson-YFP S267M ( ———— ) Chrimson-YFP Y268F ( ———— ), Chrimson-YFP Y261F ( ———— ), Chrimson-YFP S267M/Y268F ( ———— ) Chrimson-YFP Y261F/S267M ( ———— ) Chrimson-YFP K176R/S267M/Y268F ( ———— ) Chrimson-YFP Y261F/S267M/Y268F ( ———— ) Chrimson-YFP K176R/Y261F/S267M ( ———— ) or Chrimson-YFP K176R/Y261F/S267M/Y268F ( ———— ) were investigated by patch-clamp measurements in the whole cell configuration as described in the Examples below. The currents were normalized for comparison.

The results are shown in FIGS. 1 and 2, and summarized in Table 1 below.

TABLE 1

Off-kinetics ($T_{off}$) and current density ($J_{-60\ mV}$) of Chrimson and Chrimson mutants heterologously expressed in NG108-15 cells. Shown are the average $T_{off}$ values (n = 3-7), the average current densities (n = 7-11) and the corresponding standard deviations.

| Chrimson variant | $\tau_{off}$ [ms] | $J_{-60mV}$ [pA/pF] |
|---|---|---|
| Wt | 24.6 ± 0.9 | 24.0 ± 6.8 |
| K176R | 12.2 ± 0.8 | 10.1 ± 6.9 |
| S267M | 12.1 ± 1.5 | 22.6 ± 13.3 |
| Y268F | 11.3 ± 1.0 | 3.5 ± 1.6 |
| Y261F | 9.7 ± 1.5 | 33.3 ± 8.6 |
| S267M/Y268F | 6.3 ± 1.0 | 10.8 ± 5.9 |
| Y261F/S267M | 5.7 ± 0.5 | 34.2 ± 12.7 |
| K176R/S267M/Y268F | 4.9 ± 0.5 | 4.7 ± 2.7 |
| Y261F/S267M/Y268F | 3.5 ± 0.5 | 6.0 ± 4.7 |
| K176R/Y261F/S267M | 2.7 ± 0.3 | 8.3 ± 5.3 |
| K176R/Y261F/S267M/Y268F | 2.8 ± 0.3 | 2.6 ± 0.9 |

As can be taken from the above data, mutations at positions corresponding to positions 267, 268, and 261 are capable of accelerating the off-kinetics ($T_{off}$) of Chrimson. The combination of the mutations leads to a further acceleration of the off-kinetics ($T_{off}$) of Chrimson. The mutations can be advantageously combined with each other or with the known K176R mutation.

Example 2—Action Spectra of Chrimson Mutants in NG108-15 Cells

Action spectra of Chrimson and Chrimson mutants were investigated by patch-clamp measurements in the whole cell configuration at a clamped potential of −60 mV. The bath solution contained 140 mM NaCl, 2 mM $CaCl_2$, 2 mM $MgCl_2$, 10 mM HEPES, pH 7.4 and the pipette solution contained 110 mM NaCl, 2 mM $MgCl_2$, 10 mM EGTA, 10 mM HEPES, pH 7.4. The light-pulses with a pulse length of 7 ns were generated with the Opolette 355 tunable laser system (OPTOPRIM). For the recordings of the action spectra the pulse energies at the different wavelengths were set to values which corresponded to equal photon counts of $10^{18}$ photons/$m^2$ for Chrimson wt and $10^{19}$ photons/$m^2$ for the Chrimson mutants.

Figure 3:
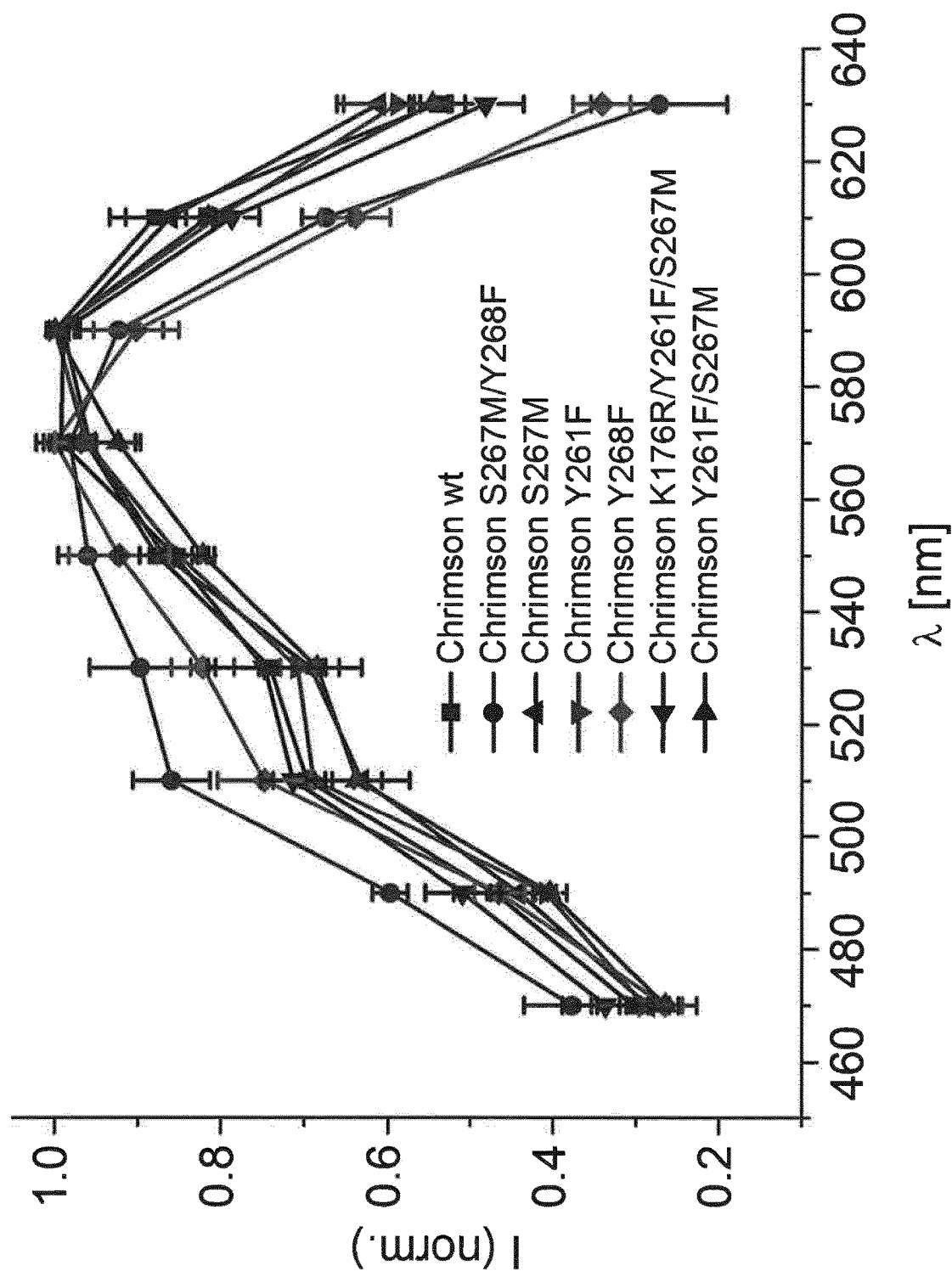
FIG. 3: Actionspectra of Chrimson and Chrimson mutants. Shown are formed peak currents in response to ns light-pulses of indicated wavelength. NG108-15 cells which were heterologously expressing Chrimson-YFP ( —■— , n=6), Chrimson-YFP S267M/Y268F ( —●— , n=3), Chrimson-YFP S267M ( —▲— , n=3), Chrimson-YFP Y261F ( —▼— , n=4), Chrimson-YFP Y268F ( —♦— , n=5), Chrimson-YFP K176R/Y261F/S267M ( —◄— , n=4) or Chrimson-YFP Y261F/S267M ( —►— , n=4) were investigated by patch-clamp measurements in the whole cell configuration as further described in the examples below.

The results are shown in FIG. 3. The Y268F mutation creates a hypsochromic shift of the action spectrum ($\gamma_{max}$=580 nm). Of note, the action spectra of the tested Chrimson mutants not carrying the Y268F mutation are not significantly shifted compared to the action spectrum of wild-type Chrimson ($\gamma_{max}$=590 nm).

Example 3—Chrimson Mutants Show Increased Spiking Frequency in Rat Hippocampal Neurons To test the Chrimson mutant's suitability for neuronal application, the construct was expressed in cultured rat hippocampal neurons.

Hippocampal Neuron Culture.

Hippocampi were isolated from postnatal P1 Sprague-Dawley rats (Jackson Laboratory) and treated with papain (20 U $ml^{-1}$) for 20 min at 37° C. The hippocampi were washed with DMEM (Invitrogen/Gibco, high glucose) supplemented with 10% fetal bovine serum and triturated in a small volume of this solution. ~75,000 cells were plated on poly-D-lysine/laminin coated glass cover slips in 24-well plates. After 3 hours the plating medium was replaced by culture medium (Neurobasal A containing 2% B-27 supplement, 2 mM Glutamaxl).

Rat hippocampal neurons heterologously expressing Chrimson-YFP, Chrimson-YFP Y261F/S267M and Chrimson-YFP K176R/Y261F/S267M were investigated by patch-clamp experiments in the whole cell configuration at a clamped potential of −70 mV. Heterologous expression of wild-type Chrimson, or the respective Chrimson mutants was accomplished by transduction with adeno-associated viruses 14 to 21 days prior to the measurements.

Briefly, 1×10⁹ genome copies/ml (GC/ml) of virus was added to each well 4-9 days after plating. Expression became visible 5 days post-transduction. No neurotoxicity was observed for the lifetime of the culture (~5 weeks). No all-trans retinal was added to the culture medium or recording medium for any of the experiments described here.

Adeno-Associated Virus (AAV2/1).

rAAV2/1 virus was prepared by the lab of Dr. Botond Roska, FMI, Basel using a pAAV2 vector with a human synapsin promoter ([16]) containing Chrimson-YFP wild-type or Chrimson-YFP mutants. The virus titer was nominally $1×10^{12}$-$1×10^{13}$ GC/ml Electrophysiological Recordings from Hippocampal Neurons.

For whole-cell recordings in cultured hippocampal neurons, patch pipettes with resistances of 3-8 MΩ were filled with 129 mM potassium gluconate, 10 mM HEPES, 10 mM KCl, 4 mM MgATP and 0.3 mM Na$_3$GTP, titrated to pH 7.2. Tyrode's solution was employed as the extracellular solution (125 mM NaCl, 2 mM KCl, 2 mM CaCl$_2$, 1 mM MgCl$_2$, 30 mM glucose and 25 mM HEPES, titrated to pH 7.4). Recordings were conducted in the presence of the excitatory synaptic transmission blockers, 1,2,3,4-tetrahydro-6-nitro-2,3-dioxo-benzo[f]quinoxaline-7-sulfonamide (NBQX, 10 µM, Sigma) and D(-)-2-Amino-5-phosphonopentanoic acid (AP-5, 50 µM, Sigma). For determination of $T_{off}$ and $J_{-70\ mV}$ measurements were conducted in the presence of 1 µM TTX in addition.

Electrophysiological signals were amplified using an Axopatch 200B amplifier (Axon Instruments, Union City, Calif.), filtered at 10 kHz, digitized with an Axon Digidata 1322A (50 Hz) and acquired and analyzed using pClamp9 software (Axon Instruments).

The action potentials were triggered by 40 light-pulses at indicated frequencies. The light pulses had a pulse width of 3 ms, a wavelength of λ=594 nm and a saturating intensity of 11-30 mW/mm$^2$.

The $T_{off}$ value was determined by a fit of the currents after cessation of illumination to a monoexponential function. The current density ($J_{-70\ mV}$) was determined by dividing the stationary current in response to a 500 ms light pulse with a saturating intensity of 20-40 mW/mm$^2$ and a wavelength of 594 nm by the capacitance of the cell. In order to determine the lowest light intensity required to induce action potentials with a probability of 100% ($J_{100}$) 40 pulses (λ=594 nm, pulse width=3 ms, v=10 Hz) of varying light intensities were applied. The spike probability was calculated by dividing the number of light-triggered spikes by the total number of light pulses.

Figure 4:
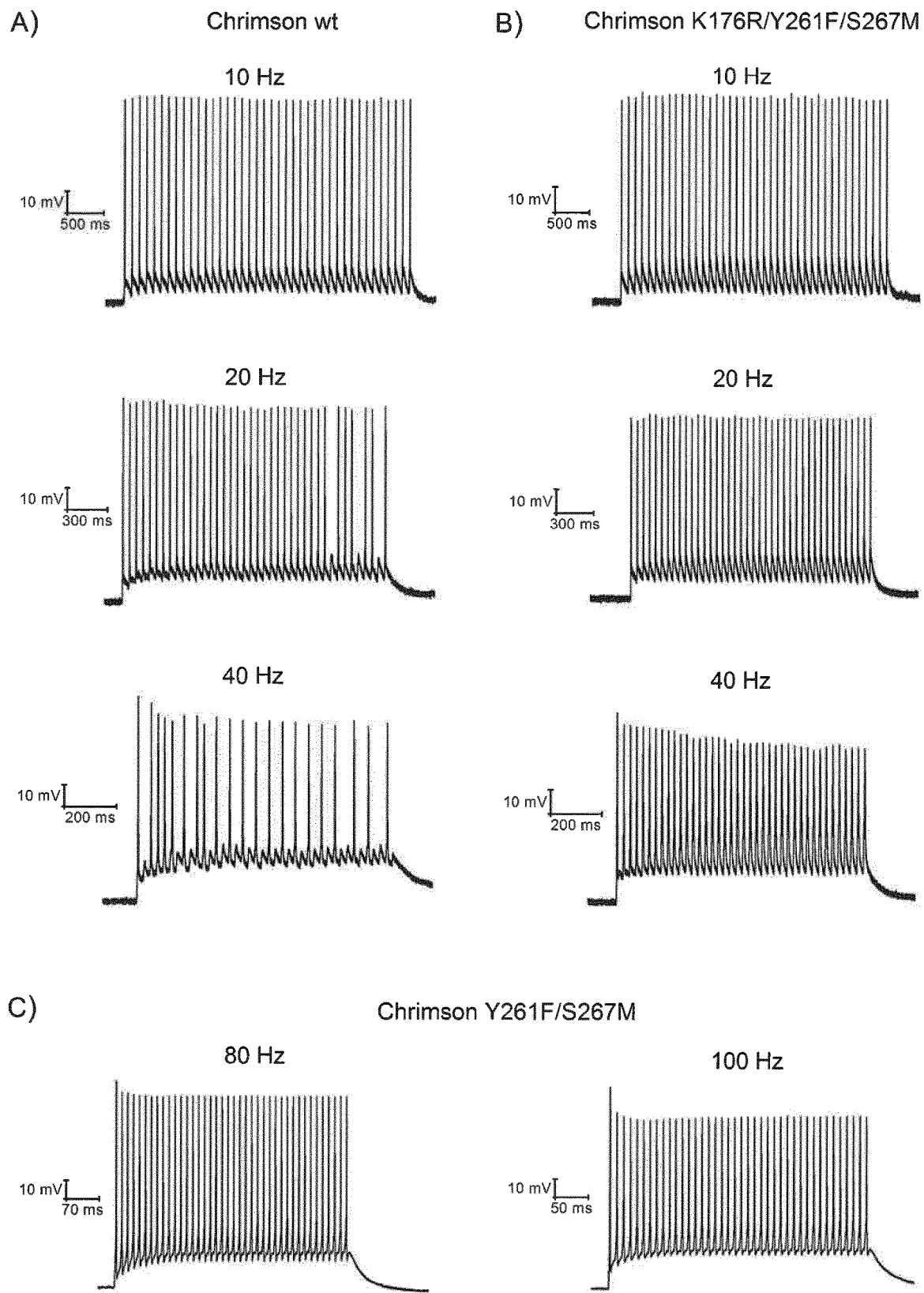
FIG. 4: Spiking traces at different light-pulse frequencies. Rat hippocampal neurons heterologously expressing A) Chrimson-YFP, B) Chrimson-YFP K176R/Y261F/S267M and C) Chrimson-YFP Y261F/S267M were investigated by patch-clamp experiments in the whole cell configuration, as further described in the examples below.

The results are shown in FIG. 4. While rat hippocampal neurons expressing wild-type Chrimson were not capable of inducing action potentials with 100% probability at frequencies above 10 Hz (cf. FIG. 4A), the Chrimson mutants Y261F/S267M (not shown) and K176R/Y261F/S267M (cf. FIG. 4B) were capable of properly inducing action potentials at 20 Hz and 40 Hz. Furthermore the Chrimson mutants K176R/Y261F/S267M (not shown) and Y261F/S267M (cf. FIG. 4C) were even able to properly induce action potentials at frequencies as high as 80-100 Hz. These measurements clearly demonstrate that the fast Chrimson mutants of the present disclosure enable rapid neural photostimulation. The measured characteristics of the Chrimson mutant K176R/Y261F/S267M, and the Chrimson mutant Y261F/S267M heterologously expressed in rat hippocampal neurons as compared to wild-type Chrimson are shown in Table 2 below.

TABLE 2

Off kinetics ($T_{off}$), current density ($J_{-70\ mV}$) and the lowest light intensity required to induce action potentials with a probability of 100% ($J_{100}$). Shown are the average $T_{off}$ (n = 3-11), the average $J_{-70\ mV}$ (n = 10-14), the average $J_{100}$ (n = 7) and the corresponding standard deviations.

| Chrimson variant | $\tau_{off}$ [ms] | $J_{-70\ mV}$ [pA/pF] | $J_{100}$ [mW mm$^{-2}$] | $<J_{100}>$ [mW mm$^{-2}$] |
|---|---|---|---|---|
| Wt | 35.1 ± 9.4 | 40.3 ± 14.3 | 0.09-0.70 | 0.28 ± 0.19 |
| Y261F/S267M | 4.7 ± 1.8 | 29.9 ± 15.9 | 0.37-1.13 | 0.64 ± 0.26 |
| K176R/Y261F/S267M | 3.8 ± 0.4 | 26.5 ± 9.9 | 0.09-0.88 | 0.46 ± 0.30 |

As shown in Table 2 the off-kinetics ($T_{off}$) are significantly accelerated in the Chrimson mutant K176R/Y261F/S267M and the Chrimson mutant Y261F/S267M as compared to wild-type. Thereby the current densities ($J_{-70\ mV}$) of Chrimson Y261F/S267M and Chrimson K176R/Y261F/S267M are only slightly reduced compared with wild-type Chrimson. The robust expression in rat hippocampal neurons enables neural photostimulation at low light intensities. These data confirm the faster kinetics as observed in NG108-15 cells (Table 1) and explain the capability of precisely inducing action potentials at high frequencies, as shown in FIG. 4 herein.

Example 4 Optogenetic Stimulation of the Auditory Pathway

Figure 5:
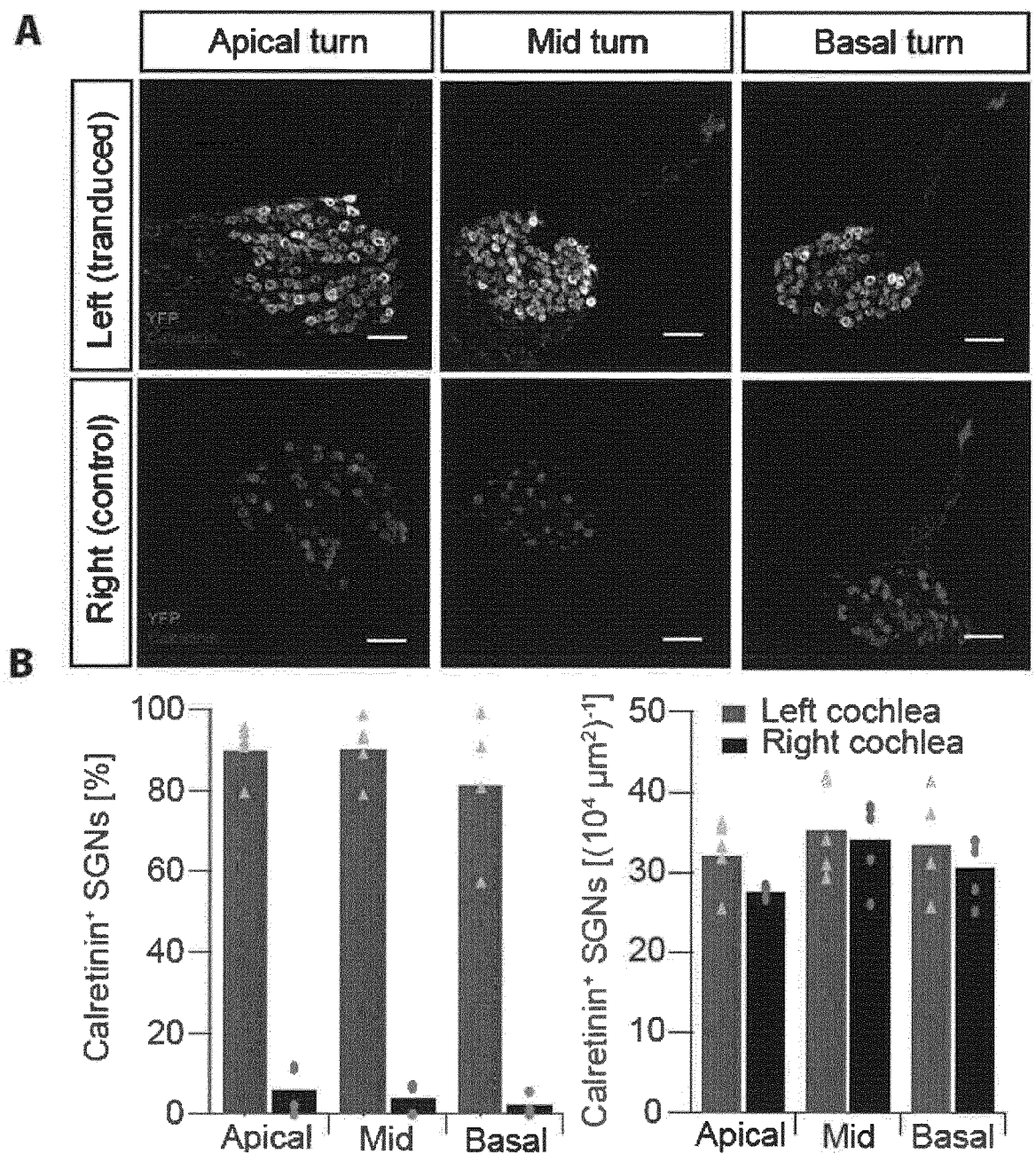
FIG. 5: Postnatal transduction of SGNs with AAV2/6-hSyn-Chrimson-YFP Y261F/S267M is highly efficient and mostly specific to the injected ear. A: Confocal images shown as maximum intensity projections (Z-step: 1 μm) of YFP and calretinin immunofluorescence in three different regions of the spiral ganglion. Scale bar: 50 μm. B: Quantification of YFP expression in SGNs calculated as a ratio to calretinin$^+$ SGNs (left panel) and SGNs viability shown as cells/10$^4$ μm$^2$ (right panel). Symbols mark results from individual animals. Grey and black bars represent average values from the left (injected) and from the right (control) *cochleae*. No statistically significant differences were found within the same group (injected or control) in both quantifications, neither between groups for the same cochlear region in the cell viability quantification (t-test, p>0.05).
Figure 6:
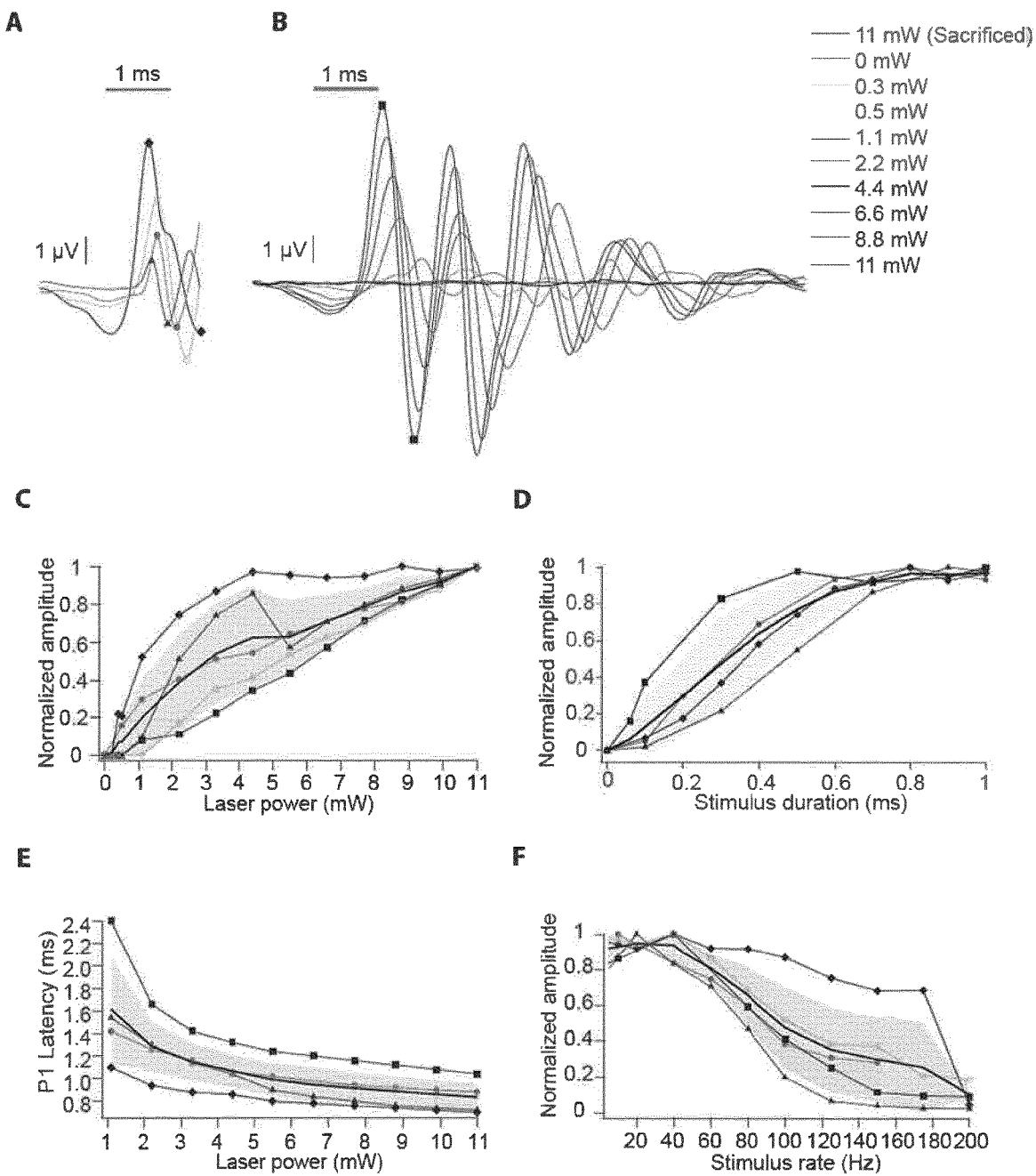
FIG. 6: Chrimson-YFP Y261F/S267M enables optogenetic coding of information at physiological rates of hundreds per second. A: oABR traces (0-2.5 ms) from 4 mice injected with AAV6-Chrimson-YFP Y261F/S267M using a 594 nm light stimulus at maximum intensity (11 mW, 1 ms at 10 Hz). B: oABR traces (0-8 ms) from an exemplary mouse injected with AAV6-Chrimson-YFP Y261F/S267M recorded at increasing laser intensities (1 ms at 10 Hz). Symbols mark P1 and N1 (landmarks for response quantification) on oABR traces (A, B), and help identifying data points from the same mouse through A-F. C: Increase in P1-N1 amplitude (normalized for maximum amplitude) with increasing laser intensity (1 ms at 10 Hz). Group average is shown in black. D: Increase in P1-N1 amplitude (normalized for maximum amplitude) with increasing light pulse duration (5.5 mW at 10 Hz for the animal marked with filled circles, 11 mW at 20 Hz for the rest). Group average is shown in black. E: Decrease in P1 latency with increasing laser intensity (1 ms at 10 Hz). Group average is shown in black. F: Decrease in P1-N1 amplitude (normalized for maximum amplitude) with increasing stimulus rate (5.5 mW, 1 ms for the animals marked with diamonds and empty circles; 6.6 mW, 1 ms for the rest). Group average is shown in black. Shaded area in C-F indicate +/−standard deviation.

Optogenetic stimulation of the auditory nerve promises a major advance in sound coding by auditory prostheses such as the cochlear implant and the auditory brainstem implant. Because light can be conveniently focused, an optical auditory prosthesis promises much improved frequency resolution of coding. One of the limitations of currently available optogenetic tools is slow kinetics relative to the speed of auditory signal processing. Here, the potential of the rapidly gating Chrimson-YFP Y261F/S267M for cochlear optogenetics was tested using postnatal AAV-mediated transduction of SGNs in mice, applying the system previously described in Hernandez et al. J Clin Invest. 2014; 124(3): 1114-29. AAV2/6-hSyn-Chrimson-YFP Y261F/S267M was injected into the scala tympani via the round window in p3 mice and analyzed expression and function 4-8 weeks after injection. The injected mice did not show any overt phenotype in the colony. Chrimson-YFP Y261F/S267M expression and SGN density was analyzed using immunohistochemistry on cryosections and confocal imaging of YFP and calretinin immunofluorescence of the injected and non-injected ears (FIG. 5A, 5B). Every injected ear showed Chrimson-YFP Y261F/S267M that nearly 90% of the SGNs were transduced in the injected ear (compared to less than 5% in the non-injected ear) in all cochlear turns and SGN density was not significantly altered (FIG. 1B). The transduction rates were much higher than those achieved in our previous study with transuterine injection of AAV2/6-hSyn-CatCh-YFP (Hernandez et al., 2014) and unlike there, independent from tonotopic position. A posterior tympanotomy was performed and a 50 µm optical fiber was inserted through the round window to project the light of a 595 nm continuous wave laser on the SGN of the basal turn. We could readily elicit optical auditory brainstem responses (oABR, FIG. 6A) that were similar in amplitude and waveform to acoustic ABR (aABR). oABR amplitude grew and oABR latency got shorter with increasing light intensity (FIG. 6B, 6E). Stimuli as low as 0.5 mW (FIG. 6C, stimulus duration: 1 ms, stimulus rate: 10 s$^{-1}$) and as short as 80 µs (FIG. 6D, stimulus intensity: 11 mW, stimulus rate: 10 s$^{-1}$) were sufficient to drive oABRs. Amplitudes and waveforms of oABRs varied among the different animals (FIG. 6A) but typically varied for changes in light intensity of more than one order (FIG. 6C, output dynamic range >20 dB). oABR amplitudes decreased when decreasing stimulus duration (FIG. 6D) or raising the stimulus rates, but oABR up to 200 Hz were found (FIG. 6F). It is noted that oABR reflect a population response that extends in time over 5-7 ms and hence assume that response might have been attenuated by interaction between subsequent stimuli. It is concluded that Chrimson-YFP Y261F/S267M mediated cochlear optogenetics can drive SGNs at 175 Hz or higher, which is well in range of physiological sound-driven SGN firing rates (Liberman, M. C., J. Acoust. Soc. Am. 63, 442-455 (1978); Winter, et al., Hear. Res. 45, 191-202 (1990)). In summary, postnatal transduction of SGNs has been efficiently established, and achieved SGN firing at low light intensity and for brief stimuli. It is anticipated that Chrimson-YFP Y261F/S267M, which provides sufficient temporal fidelity and also is superior to blue channelrhodopsins for deeper light penetration and less scattering in the tissue as well as less risk of phototoxicity, will become a valuable tool for optogenetic hearing restoration and auditory research.

Introducing the helix 6 motif or any other mutation disclosed herein into the constructs as described, e.g., by Hernandez et al. represents routine practice. Alternatively, one may simply replace the coding sequence of the channelrhodopsin in the conctructs by the coding sequence for the light-inducible ion channel of the present disclosure.

Example 5 Optogenetic Approach for the Recovery of Vision

Mace et al. Mol Ther. 2015; 23(1):7-16, is an earlier publication authored by some of the inventors describing optogenetic reactivation of retinal neurons mediated by adeno-associated virus (AAV) gene therapy. Most inherited retinal dystrophies display progressive photoreceptor cell degeneration leading to severe visual impairment. Optogenetic reactivation of retinal neurons mediated by adeno-associated virus (AAV) gene therapy has the potential to restore vision regardless of patient-specific mutations. The challenge for clinical translatability is to restore a vision as close to natural vision as possible, while using a surgically safe delivery route for the fragile degenerated retina. To preserve the visual processing of the inner retina, ON bipolar cells are targeted, which are still present at late stages of disease. For safe gene delivery, a recently engineered AAV variant is used that can transduce the bipolar cells after injection into the eye's easily accessible vitreous humor. It is shown that AAV encoding channelrhodopsin under the ON bipolar cell-specific promoter mediates long-term gene delivery restricted to ON-bipolar cells after intravitreal administration. Channelrhodopsin expression in ON bipolar cells leads to restoration of ON and OFF responses at the retinal and cortical levels. Moreover, light-induced locomotory behavior is restored in treated blind mice.

Introducing the helix 6 motif identified herein into the constructs as described, e.g., by Macé et al. represents routine practice. Alternatively, one may simply replace the coding sequence of the channelrhodopsins in the constructs by the coding sequence for the light-inducible ion channel of the present disclosure. The new light-inducible ion channels of the present disclosure are inserted in the cassettes for the activation of ON bipolar cells as well as for the Ganglion cells in the retina.

LIST OF REFERENCES

US 2016/0039902
WO 03/084994
WO 2012/032103
WO 2013/071231

1. Nagel, G. et al. Channelrhodopsin-2, a directly light-gated cation-selective membrane channel. *Proc Natl Acad Sci USA* 100, 13940-13945 (2003).
2. Nagel, G. et al. Light activation of channelrhodopsin-2 in excitable cells of *Caenorhabditis elegans* triggers rapid behavioral responses. *Curr Biol* 15, 2279-2284 (2005).
Boyden, E., Zhang, F., Bamberg, E., Nagel, G. & Deisseroth, K. Millisecond-timescale, genetically targeted optical control of neural activity. *Nat Neurosci* 8, 1263-1268 (2005).
4. Zhang, F. et al. Multimodal fast optical interrogation of neural circuitry. *Nature* 446, 633-639 (2007).
5. Nagel, G. et al. Channelrhodopsin-1: A Light-Gated Proton Channel in Green Algae. Science. 296, 2395-2398 (2002).
6. Bamann, C., Gueta, R., Kleinlogel, S., Nagel, G. & Bamberg, E. Structural guidance of the photocycle of channelrhodopsin-2 by an interhelical hydrogen bond. *Biochemistry* 49, 267-278 (2010).
7. Berndt, A., Yizhar, O., Gunaydin, L., Hegemann, P. & Deisseroth, K. Bi-stable neural state switches. *Nat Neurosci* 12, 229-234 (2009).
8. Lin, J., Lin, M., Steinbach, P. & Tsien, R. Characterization of engineered channelrhodopsin variants with improved properties and kinetics. *Biophys J* 96, 1803-1814 (2009).
9. Klapoetke N. et al. Independent optical excitation of distinct neural populations. Nature Methods. 11, 338-346 (2014).
10. Allocca, M. et al. Novel adeno-associated virus serotypes efficiently transduce murine photoreceptors. *J Virology* 81, 11372-11380 (2007).
11. Hernandez et al. Optogenetic stimulation of the auditory pathway. J Clin Invest. 124(3): 1114-1129 (2014).
12. Liberman, M. C. Auditory-nerve response from cats raised in a low-noise chamber. *J. Acoust. Soc. Am.* 63, 442-455 (1978).
13. Winter, I. M., Robertson, D., and Yates, G. K. Diversity of characteristic frequency rate-intensity functions in guinea pig auditory nerve fibres. *Hear. Res.* 45, 191-202 (1990).
14. Macé et al. Targeting channelrhodopsin-2 to ON-bipolar cells with vitreally administered AAV Restores ON and OFF visual responses in blind mice. Mol Ther. 23(1): 7-16 (2015).
15 Müller, M., Bamann, C., Bamberg, E. & Kuhlbrandt, W. Light-induced helix movements in channelrhodopsin-2. *J Mol Biol* 427, 341-349, doi:10.1016/j.jmb.2014.11.004 (2015).
16 Lin J. Y. et al. ReAChR: a red-shifted variant of channelrhodopsin enables deep transcranial optogenetic excitation. Nature Neuroscience. 16, 1499-1508 (2013).
17 Kato, H. E. et al. Crystal structure of the channelrhodopsin light-gated cation channel. *Nature* 482, 369-374, doi:10.1038/nature10870 (2012).

The invention claimed is:

1. A mutant light-inducible ion channel, wherein the mutant light-inducible ion channel comprises an amino acid sequence selected from the group consisting of A and B:
   A: an amino acid sequence which has at least 95% identity to the full length sequence of SEQ ID NO: 1 (Chrimson),
      wherein the mutant light-inducible ion channel only differs from its parent light-inducible ion channel by a substitution at one or more position(s) selected from the positions corresponding to Y261, Y268, and S267 in SEQ ID NO: 1,
      which substitution(s) accelerate(s) the off-kinetics of the mutant channel as compared to the parent channel, when compared by patch-clamp measurements in the whole cell configuration at a clamp potential of −60 mV, a bath solution of 140 mM NaCl, 2 mM CaCl$_2$, 2 MgCl$_2$, 10 mM HEPES, pH 7.4, and a pipette solution of 110 mM NaCl, 2 mM MgCl$_2$, 10 mM EGTA, 10 mM HEPES, pH 7.4; and
   B: an amino acid sequence identical to the sequence of SEQ ID NO: 2 (CsChrimson), except for a substitution at one or more amino acid position(s) selected from the positions corresponding to Y261, Y268, and S267 in SEQ ID NO: 1, and optionally an Arg at the position corresponding to K176 of SEQ ID NO: 1; and
   wherein said substitution at one or more position(s) selected from the positions corresponding to Y261, Y268, and S267 in SEQ ID NO: 1 is one or more of the following:
   a Phe at the amino acid position corresponding to position Y261 of SEQ ID NO: 1;
   a Phe at the amino acid position corresponding to position Y268 of SEQ ID NO: 1;
   a Met at the amino acid position corresponding to position S267 of SEQ ID NO: 1.

2. The mutant light-inducible ion channel of claim 1, wherein the amino acid sequence comprised by the mutant light-inducible ion channel has at least 96%, at least 97%, at least 98%, or at least 99% identity to the full length of SEQ ID NO: 1 (Chrimson).

3. The mutant light-inducible ion channel of claim 1, wherein the mutant light-inducible ion channel comprises a Phe at the amino acid positions corresponding to position Y261 and a Met at the amino acid position corresponding to position S267 of SEQ ID NO: 1; or
   wherein the mutant light-inducible ion channel comprises a Phe at the amino acid positions corresponding to position Y268 and a Met at the amino acid position corresponding to position S267 of SEQ ID NO: 1.

4. The mutant light-inducible ion channel of claim 1, wherein the mutant light-inducible ion channel comprises a Phe at the amino acid positions corresponding to position Y261, a Phe at the amino acid position corresponding to position Y268, and a Met at the amino acid position corresponding to position S267 of SEQ ID NO: 1.

5. The mutant light-inducible ion channel of claim 1, further comprising an Arg at the position corresponding to position 176 of SEQ ID NO: 1.

6. The mutant light-inducible ion channel of claim 1, wherein the mutant channel comprises the motif of SEQ ID NO: 3:
   Cys-Arg-Met-Val-Val-Lys-Leu-Met-Ala-Tyr-Ala-Xaa$_{12}$-Phe-Ala-Ser-Trp-Gly-Xaa$_{18}$-Xaa$_{19}$-Pro-Ile-Leu-Trp-Ala-Val,
   wherein Xaa$_{12}$ is Phe;
   wherein Xaa$_{18}$ is Met; and
   wherein Xaa$_{19}$ is Phe or Tyr.

7. The mutant light-inducible ion channel of claim 1, wherein the mutant light-inducible ion channel comprises the amino acid sequence of SEQ ID NO: 1 (Chrimson), except for said substitution(s) at position Y261, Y268, and S267, and optionally the Arg at the position corresponding to position 176 of SEQ ID NO: 1.

8. The mutant light-inducible ion channel of claim 1, wherein the mutant light-inducible ion channel is a red light absorbing channelrhodopsin.

9. A nucleic acid construct, comprising a nucleotide sequence coding for a mutant light-inducible ion channel, wherein the mutant light-inducible ion channel comprises an amino acid sequence selected from the group consisting of A and, B and a combination thereof:
   A: an amino acid sequence which has at least 95% identity to the full length sequence of SEQ ID NO: 1 (Chrimson),
      wherein the mutant light-inducible ion channel only differs from its parent light-inducible ion channel by a substitution at one or more position(s) selected from the positions corresponding to Y261, Y268, and S267 in SEQ ID NO: 1,
      which substitution(s) accelerate(s) the off-kinetics of the mutant channel as compared to the parent channel, when compared by patch-clamp measurements in the whole cell configuration at a clamp potential of −60 mV, a bath solution of 140 mM NaCl, 2 mM CaCl$_2$), 2 MgCl$_2$, 10 mM HEPES, pH 7.4, and a pipette solution of 110 mM NaCl, 2 mM MgCl$_2$, 10 mM EGTA, 10 mM HEPES, pH 7.4; and
   B: an amino acid sequence identical to the sequence of SEQ ID NO: 2 (CsChrimson), except for a substitution at one or more amino acid position(s) selected from the positions corresponding to Y261, Y268, and S267 in SEQ ID NO: 1, and optionally an Arg at the position corresponding to K176 of SEQ ID NO: 1; and
   wherein said substitution at one or more position(s) selected from the positions corresponding to Y261, Y268, and S267 in SEQ ID NO: 1 is one or more of the following:
   a Phe at the amino acid position corresponding to position Y261 of SEQ ID NO: 1;
   a Phe at the amino acid position corresponding to position Y268 of SEQ ID NO: 1;
   a Met at the amino acid position corresponding to position S267 of SEQ ID NO: 1.

10. An expression vector, comprising a nucleotide sequence coding for a light-inducible ion channel, wherein the mutant light-inducible ion channel comprises an amino acid sequence selected from the group consisting of A and, B and a combination thereof:
    A: an amino acid sequence which has at least 95% identity to the full length sequence of SEQ ID NO: 1 (Chrimson),
       wherein the mutant light-inducible ion channel only differs from its parent light-inducible ion channel by a substitution at one or more position(s) selected from the positions corresponding to Y261, Y268, and S267 in SEQ ID NO: 1,
       which substitution(s) accelerate(s) the off-kinetics of the mutant channel as compared to the parent channel, when compared by patch-clamp measurements in the whole cell configuration at a clamp potential of −60 mV, a bath solution of 140 mM NaCl, 2 mM CaCl$_2$), 2 MgCl$_2$, 10 mM HEPES, pH 7.4, and a pipette solution of 110 mM NaCl, 2 mM MgCl$_2$, 10 mM EGTA, 10 mM HEPES, pH 7.4; and B: an amino acid sequence identical to the sequence of SEQ ID NO: 2 (CsChrimson), except for a substitution at one or more amino acid position(s) selected from the positions corresponding to Y261, Y268, and S267 in SEQ ID NO: 1, and optionally an Arg at the position corresponding to K176 of SEQ ID NO: 1; and wherein said substitution at one or more position(s) selected from the positions corresponding to Y261, Y268, and S267 in SEQ ID NO: 1 is one or more of the following:

a Phe at the amino acid position corresponding to position Y261 of SEQ ID NO: 1;

a Phe at the amino acid position corresponding to position Y268 of SEQ ID NO: 1;

a Met at the amino acid position corresponding to position S267 of SEQ ID NO: 1.

11. A cell comprising the nucleic acid construct according to claim 10.

12. A high-throughput screening method comprising the following steps:
   (i) providing a cell expressing a Ca++-inducible potassium channel and the light-inducible ion channel of claim 1,
   (ii) applying a light stimulus in order to induce the light-inducible ion channel,
   (iii) determining the alteration of the membrane potential, and
   (iv) comparing the signal determined in step (iii) with the signal determined in a cell in the presence of a candidate agent directed against the Ca++-inducible potassium channel subjected to step (ii),
   wherein a difference in the change of the membrane potential is indicative of the candidate agent being a modulator of the Ca++-inducible potassium channel.

13. A method for light-stimulation of neuron cells comprising applying a light stimulus to a cell comprising a light-inducible ion channel according to claim 1.

14. A non-human animal, comprising a light-inducible ion channel according to claim 1.

15. The cell according to claim 11, wherein the cell is a mammalian cell.

16. The cell according to claim 15, wherein the cell is selected from the group consisting of
   (a) a hippocampal cell, a photoreceptor cell, a retinal rod cell, a retinal cone cell, a retinal ganglion cell, a bipolar neuron, a ganglion cell, a pseudounipolar neuron, a multipolar neuron, a pyramidal neuron, a Purkinje cell, or a granule cell; and
   (b) a neuroblastoma cell, a HEK293 cell; a COS cell; a BHK cell; a CHO cell; a myeloma cell; or a MDCK cell.

17. The cell according to claim 16, wherein the cell is a NG108-15 neuroblastoma cell.

* * * * *

SEQUENCE LISTING

<160> NUMBER OF SEQ ID NOS: 10

<210> SEQ ID NO 1
<211> LENGTH: 349
<212> TYPE: PRT
<213> ORGANISM: Artificial
<220> FEATURE:
<223> OTHER INFORMATION: Chrimson derived from Chlamydomonas noctigama

<400> SEQUENCE: 1

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
        35                  40                  45

Asp Pro Ser Tyr Gly Leu Ser Asp Ala Gly Tyr Gly Tyr Cys Phe Val
    50                  55                  60

Glu Ala Thr Gly Gly Tyr Leu Val Val Gly Val Glu Lys Lys Gln Ala
65                  70                  75                  80

Trp Leu His Ser Arg Gly Thr Pro Gly Glu Lys Ile Gly Ala Gln Val
                85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
        115                 120                 125

Cys Cys Val Glu Val Leu Phe Val Thr Leu Glu Ile Phe Lys Glu Phe
130                 135                 140

Ser Ser Pro Ala Thr Val Tyr Leu Ser Thr Gly Asn His Ala Tyr Cys
145                 150                 155                 160

Leu Arg Tyr Phe Glu Trp Leu Leu Ser Cys Pro Val Ile Leu Ile Lys
                165                 170                 175

Leu Ser Asn Leu Ser Gly Leu Lys Asn Asp Tyr Ser Lys Arg Thr Met
            180                 185                 190

Gly Leu Ile Val Ser Cys Val Gly Met Ile Val Phe Gly Met Ala Ala
        195                 200                 205

Gly Leu Ala Thr Asp Trp Leu Lys Trp Leu Leu Tyr Ile Val Ser Cys
210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
                245                 250                 255

Met Ala Tyr Ala Tyr Phe Ala Ser Trp Gly Ser Tyr Pro Ile Leu Trp
            260                 265                 270

Ala Val Gly Pro Glu Gly Leu Leu Lys Leu Ser Pro Tyr Ala Asn Ser
        275                 280                 285

Ile Gly His Ser Ile Cys Asp Ile Ile Ala Lys Glu Phe Trp Thr Phe
290                 295                 300

Leu Ala His His Leu Arg Ile Lys Ile His Glu His Ile Leu Ile His
305                 310                 315                 320

Gly Asp Ile Arg Lys Thr Thr Lys Glu Ile Gly Gly Glu Glu Val Glu
                325                 330                 335

Val Glu Glu Phe Val Glu Glu Asp Glu Asp Thr Val
            340                 345

<210> SEQ ID NO 2
<211> LENGTH: 345
<212> TYPE: PRT
<213> ORGANISM: Artificial
<220> FEATURE:
<223> OTHER INFORMATION: CsChrimson

<400> SEQUENCE: 2

Met Ser Arg Leu Val Ala Ala Ser Trp Leu Ala Leu Leu Cys
1               5                   10                  15

Gly Ile Thr Ser Thr Thr Ala Ser Ser Ala Pro Ala Ala Ser Ser
            20                  25                  30

Thr Asp Gly Thr Ala Ala Ala Val Ser His Tyr Ala Met Asn Gly
            35                  40                  45

Phe Asp Glu Leu Ala Lys Gly Ala Val Val Pro Glu Asp His Phe Val
50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
                85                  90                  95

Phe Ser Ile Ala Ile Ala Leu Leu Thr Phe Tyr Gly Phe Ser Ala Trp
            100                 105                 110

Lys Ala Thr Cys Gly Trp Glu Glu Val Tyr Val Cys Cys Val Glu Val
            115                 120                 125

Leu Phe Val Thr Leu Glu Ile Phe Lys Glu Phe Ser Ser Pro Ala Thr
            130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175

Gly Leu Lys Asn Asp Tyr Ser Lys Arg Thr Met Gly Leu Ile Val Ser
                180                 185                 190

Cys Val Gly Met Ile Val Phe Gly Met Ala Ala Gly Leu Ala Thr Asp
                195                 200                 205

Trp Leu Lys Trp Leu Leu Tyr Ile Val Ser Cys Ile Tyr Gly Gly Tyr
210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
                260                 265                 270

Gly Leu Leu Lys Leu Ser Pro Tyr Ala Asn Ser Ile Gly His Ser Ile
                275                 280                 285

Cys Asp Ile Ile Ala Lys Glu Phe Trp Thr Phe Leu Ala His His Leu
290                 295                 300

Arg Ile Lys Ile His Glu His Ile Leu Ile His Gly Asp Ile Arg Lys
305                 310                 315                 320

Thr Thr Lys Met Glu Ile Gly Gly Glu Val Glu Val Glu Phe
                325                 330                 335

Val Glu Glu Glu Asp Glu Asp Thr Val
                340                 345

<210> SEQ ID NO 3
<211> LENGTH: 25
<212> TYPE: PRT
<213> ORGANISM: Artificial
<220> FEATURE:
<223> OTHER INFORMATION: Helix 6 consensus motif
<220> FEATURE:
<221> NAME/KEY: VARIANT
<222> LOCATION: (12)..(12)
<223> OTHER INFORMATION: wherein Xaa12 is Phe or Tyr, in particular
      wherein Xaa12 is Phe
<220> FEATURE:

```
<221> NAME/KEY: VARIANT
<222> LOCATION: (18)..(18)
<223> OTHER INFORMATION: wherein Xaa18 is Met or Ser, in particular
      wherein Xaa18 is Met
<220> FEATURE:
<221> NAME/KEY: VARIANT
<222> LOCATION: (19)..(19)
<223> OTHER INFORMATION: wherein Xaa19 is Phe or Tyr, in particular
      wherein Xaa19 is Phe

<400> SEQUENCE: 3

Cys Arg Met Val Val Lys Leu Met Ala Tyr Ala Xaa Phe Ala Ser Trp
1               5                   10                  15

Gly Xaa Xaa Pro Ile Leu Trp Ala Val
            20                  25

<210> SEQ ID NO 4
<211> LENGTH: 9
<212> TYPE: PRT
<213> ORGANISM: Artificial
<220> FEATURE:
<223> OTHER INFORMATION: Retinal binding site consensus motif
<220> FEATURE:
<221> NAME/KEY: VARIANT
<222> LOCATION: (1)..(1)
<223> OTHER INFORMATION: wherein Xaa1 is Leu, Ile, Ala, or Cys
<220> FEATURE:
<221> NAME/KEY: VARIANT
<222> LOCATION: (3)..(5)
<223> OTHER INFORMATION: wherein Xaa3, Xaa4, and Xaa5 is independently
      any amino acid
<220> FEATURE:
<221> NAME/KEY: VARIANT
<222> LOCATION: (7)..(8)
<223> OTHER INFORMATION: wherein Xaa7 and Xaa8 is independently any
      amino acid
<220> FEATURE:
<221> NAME/KEY: VARIANT
<222> LOCATION: (9)..(9)
<223> OTHER INFORMATION: wherein Xaa9 is Thr, Phe, or Tyr

<400> SEQUENCE: 4

Xaa Asp Xaa Xaa Xaa Lys Xaa Xaa Xaa
1               5

<210> SEQ ID NO 5
<211> LENGTH: 315
<212> TYPE: PRT
<213> ORGANISM: Chlamydomonas reinhardtii

<400> SEQUENCE: 5

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
```

```
            115                 120                 125
Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
290                 295                 300

Glu Ala Gly Ala Val Asn Lys Gly Thr Gly Lys
305                 310                 315

<210> SEQ ID NO 6
<211> LENGTH: 300
<212> TYPE: PRT
<213> ORGANISM: Volvox carteri

<400> SEQUENCE: 6

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
                20                  25                  30

Gly Trp Leu Arg Ser Arg Gly Thr Ser Ile Glu Lys Thr Ile Ala Ile
            35                  40                  45

Thr Leu Gln Trp Val Val Phe Ala Leu Ser Val Ala Cys Leu Gly Trp
50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
                100                 105                 110

Trp Met Arg Tyr Gly Glu Trp Leu Leu Thr Cys Pro Val Leu Leu Ile
            115                 120                 125

His Leu Ser Asn Leu Thr Gly Leu Lys Asp Asp Tyr Ser Lys Arg Thr
130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175
```

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
            195                 200                 205

Val Met Ala Trp Thr Phe Phe Val Ala Trp Gly Met Phe Pro Val Leu
210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
            245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
            275                 280                 285

Met Glu Val Glu Thr Leu Val Ala Glu Glu Glu Asp
            290                 295                 300

<210> SEQ ID NO 7
<211> LENGTH: 352
<212> TYPE: PRT
<213> ORGANISM: Artificial
<220> FEATURE:
<223> OTHER INFORMATION: ReaChR

<400> SEQUENCE: 7

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
        50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
            115                 120                 125

Ile Glu Met Met Lys Ser Ile Ile Glu Ala Phe His Glu Phe Asp Ser
        130                 135                 140

Pro Ala Thr Leu Trp Leu Ser Ser Gly Asn Gly Val Val Trp Met Arg
145                 150                 155                 160

Tyr Gly Glu Trp Leu Leu Thr Cys Pro Val Ile Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
            195                 200                 205

Cys Thr Gly Trp Thr Lys Ile Leu Phe Phe Leu Ile Ser Leu Ser Tyr
        210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
            245                 250                 255

Trp Leu Phe Phe Val Ser Trp Gly Met Phe Pro Val Leu Phe Leu Leu
        260                 265                 270

Gly Pro Glu Gly Phe Gly His Ile Ser Pro Tyr Gly Ser Ala Ile Gly
    275                 280                 285

His Ser Ile Leu Asp Leu Ile Ala Lys Asn Met Trp Gly Val Leu Gly
290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser Leu Glu
            340                 345                 350

<210> SEQ ID NO 8
<211> LENGTH: 315
<212> TYPE: PRT
<213> ORGANISM: Artificial
<220> FEATURE:
<223> OTHER INFORMATION: ChR2 helix 6 swap mutant

<400> SEQUENCE: 8

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Met Val Val Lys Leu Met Ala Tyr Ala Tyr Phe Ala Ser Trp Gly
    210                 215                 220

Ser Tyr Pro Ile Leu Trp Ala Val Gly Pro Glu Gly Phe Gly Val Leu
225                 230                 235                 240

Ser Val Tyr Gly Ser Thr Val Gly His Thr Ile Ile Asp Leu Met Ser
                245                 250                 255

```
Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
        290                 295                 300

Glu Ala Gly Ala Val Asn Lys Gly Thr Gly Lys
305                 310                 315

<210> SEQ ID NO 9
<211> LENGTH: 300
<212> TYPE: PRT
<213> ORGANISM: Artificial
<220> FEATURE:
<223> OTHER INFORMATION: VChR1 helix 6 swap mutant

<400> SEQUENCE: 9

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Cys Pro Val Leu Leu Ile
        115                 120                 125

His Leu Ser Asn Leu Thr Gly Leu Lys Asp Asp Tyr Ser Lys Arg Thr
130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Met Val Val Lys
        195                 200                 205

Leu Met Ala Tyr Ala Tyr Phe Ala Ser Trp Gly Ser Tyr Pro Ile Leu
210                 215                 220

Trp Ala Val Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
        275                 280                 285

Met Glu Val Glu Thr Leu Val Ala Glu Glu Asp
        290                 295                 300
```

<210> SEQ ID NO 10
<211> LENGTH: 352
<212> TYPE: PRT
<213> ORGANISM: Artificial
<220> FEATURE:
<223> OTHER INFORMATION: ReaChR helix 6 swap mutant

<400> SEQUENCE: 10

```
Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
                20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Val Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
        115                 120                 125

Ile Glu Met Met Lys Ser Ile Ile Glu Ala Phe His Glu Phe Asp Ser
130                 135                 140

Pro Ala Thr Leu Trp Leu Ser Ser Gly Asn Gly Val Val Trp Met Arg
145                 150                 155                 160

Tyr Gly Glu Trp Leu Leu Thr Cys Pro Val Ile Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Met Val Val Lys Leu Met Ala
                245                 250                 255

Tyr Ala Tyr Phe Ala Ser Trp Gly Ser Tyr Pro Ile Leu Trp Ala Val
            260                 265                 270

Gly Pro Glu Gly Phe Gly His Ile Ser Pro Tyr Gly Ser Ala Ile Gly
        275                 280                 285

His Ser Ile Leu Asp Leu Ile Ala Lys Asn Met Trp Gly Val Leu Gly
290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Glu Asp Lys Tyr Glu Ser Ser Leu Glu
            340                 345                 350
```